(12) United States Patent
Bell et al.

(10) Patent No.: US 8,704,022 B2
(45) Date of Patent: Apr. 22, 2014

(54) PROCESS FOR PRODUCING HIGH PURITY EXO-ALKENYLNORBORNENE

(75) Inventors: Andrew Bell, Lakewood, OH (US); Dane Jablonski, Brunswick, OH (US); Elaine Koronich, Novelty, OH (US); Brian Knapp, Medina, OH (US); Dino Amoroso, Whitby (CA)

(73) Assignee: Promerus, LLC, Brecksville, OH (US)

( * ) Notice: Subject to any disclaimer, the term of this patent is extended or adjusted under 35 U.S.C. 154(b) by 809 days.

(21) Appl. No.: 12/187,297

(22) Filed: Aug. 6, 2008

(65) Prior Publication Data

US 2009/0054714 A1    Feb. 26, 2009

Related U.S. Application Data

(60) Provisional application No. 60/964,130, filed on Aug. 9, 2007.

(51) Int. Cl.
*C07C 5/31*    (2006.01)

(52) U.S. Cl.
USPC ........... 585/363; 585/353; 585/354; 585/360; 585/361; 585/362; 585/371

(58) Field of Classification Search
USPC ......... 585/350, 353, 360, 363, 371, 354, 361, 585/362
See application file for complete search history.

(56) References Cited

U.S. PATENT DOCUMENTS

| | | | |
|---|---|---|---|
| 3,728,406 A * | 4/1973 | Vrinssen et al. | 585/318 |
| 4,016,212 A | 4/1977 | Leimgruber et al. | |
| 4,205,192 A | 5/1980 | Harada | |
| 5,565,069 A * | 10/1996 | Oi et al. | 203/30 |
| 5,569,804 A * | 10/1996 | Lattner et al. | 585/361 |
| 6,093,865 A * | 7/2000 | Lattner et al. | 585/361 |
| 6,175,044 B1 | 1/2001 | Therre et al. | |
| 6,294,706 B1 * | 9/2001 | Bergstrom et al. | 585/361 |
| 2002/0156334 A1 | 10/2002 | Seo | |

OTHER PUBLICATIONS

Osokin, "Vinylnorbornene: Preparation, Chemical Transformation, and Use in Organic Synthesis and Isomerization to Ethylidenenorbornene (Review)" in Petroleum Chemistry, 47(1), Jan. 11, 2007, published Feb. 2007.*
Carey, et al., Advanced Organic Chemistry: Part B, Reactions and Synthesis, 5th ed., Springer-Verlag, 2007, available on-line at www.knovel.com.*
International Search Report for International Application No. PCT/US 08/72426 mailed on Nov. 5, 2008.
Written Opinion of the International Searching Authority for International Application No. PCT/US 08/72426 mailed on Nov. 5, 2008.
Extended European Search Report for European Patent Application No. 08797347.5 mailed on Sep. 14, 2010.
Chinese Office Action for Chinese Patent Application No. 200880107390.5 mailed on Aug. 18, 2011.
Japanese Office Action for Japanese Application No. 2010-520300 mailed on Jun. 27, 2013.
Shoji Iwase, et al, Rearrangement of 5-Isoprpenyl-2-norbornene to 5-Methyl-3a, 4, 7a-tetrahydro-1 H-indene, Bulletin of the Chemical Societey of Japan, Jul. 1976, pp. 2017-2018, vol. 49-7.
Terunobu Maeda, et al., Rearrangement of 5-Vinyl-2-norbornene to 3 a, 4, 7, 7 a-Tetrahydroindene, Nippon Kagaku Kaishi, 1974, pp. 1587-1589, No. 8, Department of Applied Chemistry, Faculty of Engineering, Kansai University, Suita-shi 565 Japan.

* cited by examiner

*Primary Examiner* — In Suk Bullock
*Assistant Examiner* — Bradley Etherton
(74) *Attorney, Agent, or Firm* — Balaram Gupta

(57) ABSTRACT

Embodiments of the present invention are directed generally to methods for producing high purity exo-alkenylnorbornenes from a mixture of conformational isomers thereof.

26 Claims, No Drawings

PROCESS FOR PRODUCING HIGH PURITY EXO-ALKENYLNORBORNENE

CROSS-REFERENCE TO RELATED APPLICATIONS

This application claims the benefit of priority to U.S. Provisional Application Ser. No. 60/964,130 filed Aug. 9, 2007, the entire contents of which are hereby incorporated by reference.

FIELD OF INVENTION

Embodiments in accordance with the present invention are related generally to a process for producing high purity exo-alkenylnorbornene from a mixture of endo- and exo-alkenylnorbornene; and more specifically to such a process that employs a controlled Cope Rearrangement to convert endo-alkenylnorbornene to a material readily separable from exo-alkenylnorbornene.

BACKGROUND

Generally, alkenylnorbornenes (ANB) are commercially prepared via a Diels-Alder reaction employing cyclopentadiene (CPD) or its dimer dicyclopentadiene (DCPD), and an appropriate dienophile, for example, 1,3-butadiene (BD) where vinylnorbornene (VNB) is being prepared. As is known, the ANB product is formed as a mixture of its exo- and endo-isomers where the isomer ratio obtained for any such Diels-Alder reaction is a function of both the reaction temperature and the time the reaction mixture is held at such temperature as well as the specific reactants employed. Typical commercial VNB has been found to have an exo:endo ratio of about 1 to 3.

An analysis of the several products of a Diels-Alder reaction between BD and CPD make it possible to describe it as a set of parallel and consecutive reactions where the main products are VNB, tetrahydroindene (THI), 1,4-vinylcyclohexene (VCH), DCPD, and a mixture of several oligomeric compounds. The generation of VCH occurs either through direct dimerization of residual BD or when VNB undergoes a reverse-Diels-Alder reaction to yield BD and CPD where BD then dimerizes to yield VCH and, concomitantly, CPD dimerizes to generate dicyclopentadiene. It is believed that where other dienophiles are employed, an analogous set of parallel and consecutive reactions will result in analogous products.

Interest in obtaining the exo-isomer of VNB as well as the exo-isomers of other alkenylnorbornenes has grown recently as such isomers are promising building blocks in the synthesis of various biologically active compounds that exhibit diverse physiological activity. Additionally, it has been found that the exo and endo isomers of such monomers are different in their reactivity in polymerization processes and can provide polymers with different chemical and/or physical properties. However, as the separation of such endo- and exo-isomers by simple fractional distillation is extremely difficult, the use of individual isomers has been problematic. As VNB is the most common of the ANBs, the research directed to finding alternate methods of providing essentially pure, individual ANB isomers has focused on VNB isomers and in particular producing essentially pure exo-VNB. However, as shown below in the Comparative Example, and as there is a general absence of products that make use of the individual isomers, one might conclude that such research has not yet been successful.

DETAILED DESCRIPTION

Embodiments in accordance with the present invention provide for producing essentially pure exo-alkenylnorbornene (exo-ANB) in both high yield and in a cost-effective manner starting with an exo-/endo-alkenylnorbornene (ANB) mixture. The phrases "essentially pure" and "high purity" are used herein interchangeably and will be understood to mean a specific ANB isomer having less than 5 weight percent (wt %) of impurities. The phrase "ultra high purity" will be understood to mean a specific ANB isomer having less than 1 weight percent (wt %) of impurities. In conjunction with these phrases, such impurities are understood to be materials other than the named ANB isomer mixture or the specifically named ANB isomer, thus where an embodiment in accordance with the present invention refers to essentially pure exo-ANB, the impurities may encompass the related endo-ANB isomer as well as other materials. The terms "tight" and "heavy" when used to describe the impurities that may be found in a mixture of an alkenylnorbornene will be understood to mean impurities that have a lower or higher boiling point than the named ANB. For example, light impurities of a vinylnorbornene mixture made via a Diels-Alder reaction can encompass materials such as butadiene (BD), cyclopentadiene (CPD) and vinylcyclohexene (VCH), while the heavy impurities can encompass materials such as dicyclopentadiene (DCPD), cyclooctadiene (COD) and tetrahydroindene (THI). As will be discussed and exemplified, such embodiments provide an exo-ANB in high yield (based on the starting concentration of exo-ANB in the ANB-mixture) via a controlled thermolysis reaction that provides for the release of any light impurities or by-products of the thermolysis from the reaction system as a Cope Rearrangement of any endo-ANB isomer to the corresponding tetrahydroindene (THI) derivative occurs. It will be understood that the phrase "controlled thermolysis reaction" means a reaction where the rate is controlled by varying one or both of the reaction temperature and pressure. Advantageously, and as previously unreported, the removal of these impurities or reaction by-products results in an increased reaction rate for the Cope Rearrangement and an increase in the overall yield of the desired exo-ANB isomer.

For ease of explanation and understanding, the reaction schemes depicted immediately below (Schemes 1 and Schemes 2) are directed to embodiments in accordance with the present invention useful for obtaining high purity exo-VNB and exo-MeVNB. Thus, Schemes 1 depict the formation of exo- and endo-VNB via a Diels-Alder reaction that employs BD and CPD as starting materials and Schemes 2 depict the same where isoprene and CPD are the Diels-Alder reactants and exo- and endo-MeVNB are formed. Additionally, Schemes 1 and 2 depict many of the subsequent consecutive and parallel reactions that can occur during the Diels-Alder reaction as well as during the thermolysis reaction mentioned above. In the case of a VNB mixture, it wilt be shown herein below that embodiments in accordance with the present invention, by providing an advantageously optimized combination reaction pathway, for example (i) eliminating the BD+BD reaction that generates VCH, (ii) conserving the exo-VNB through elimination of CPD and BD reactions therewith, (iii) conserving exo-VNB by eliminating its reverse-Diels-Alder reaction, and (iv) ensuring that the conversion of endo-VNB to THI is complete in the reactor, achieve an overall high yield of high purity exo-VNB. Additionally, it will be shown that such optimized reactions can also be provided for other isomeric mixtures of alkenylnorbornenes to allow a similar overall high yield of a high purity exo-ANB, for example exo-MeVNB. Further still, it wilt be understood that through the teachings herein, one of ordinary skill in the art wilt be able to obtain high yields of appropriate C4-C12 exo-alkenylnorbornenes.

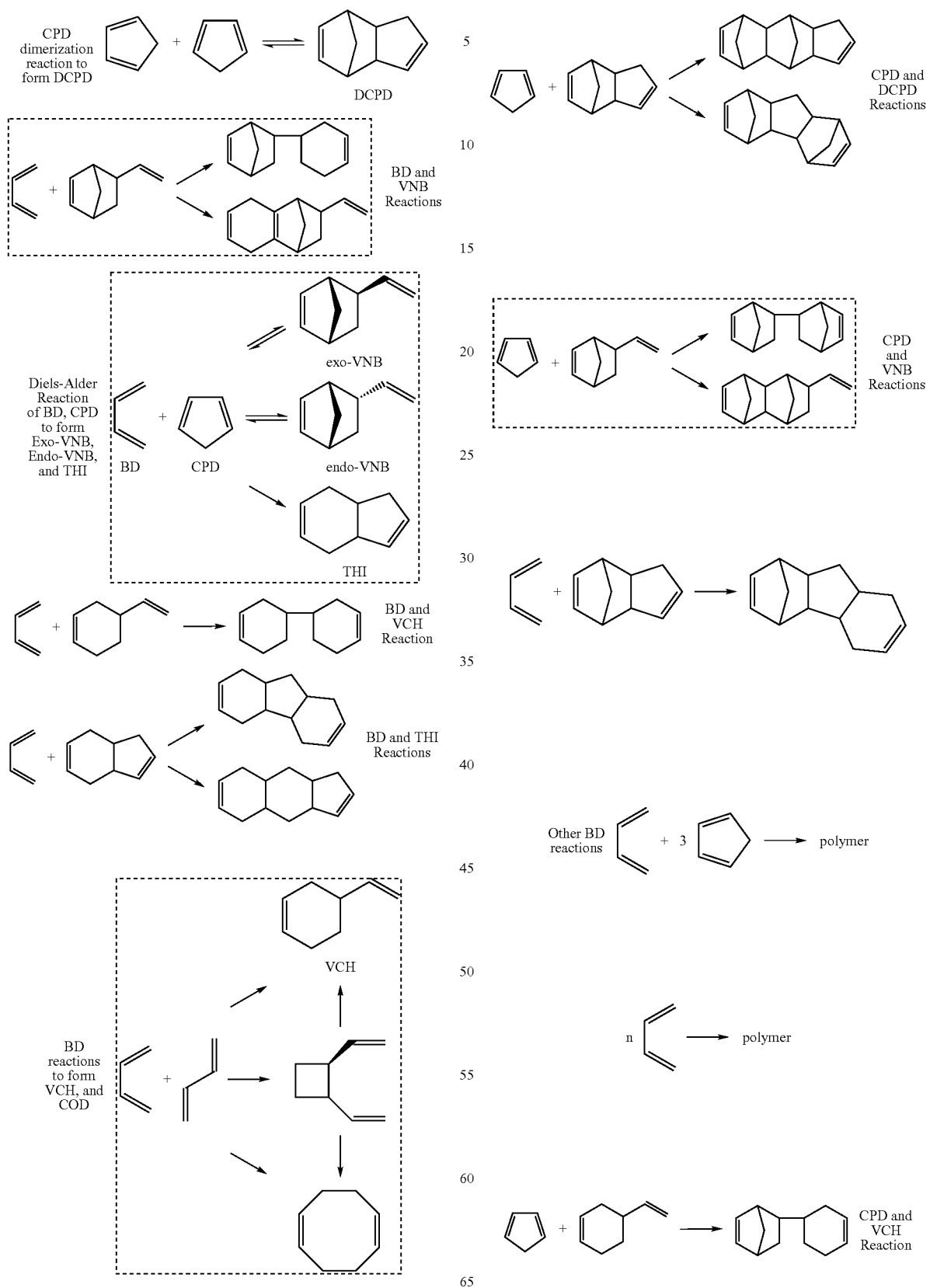

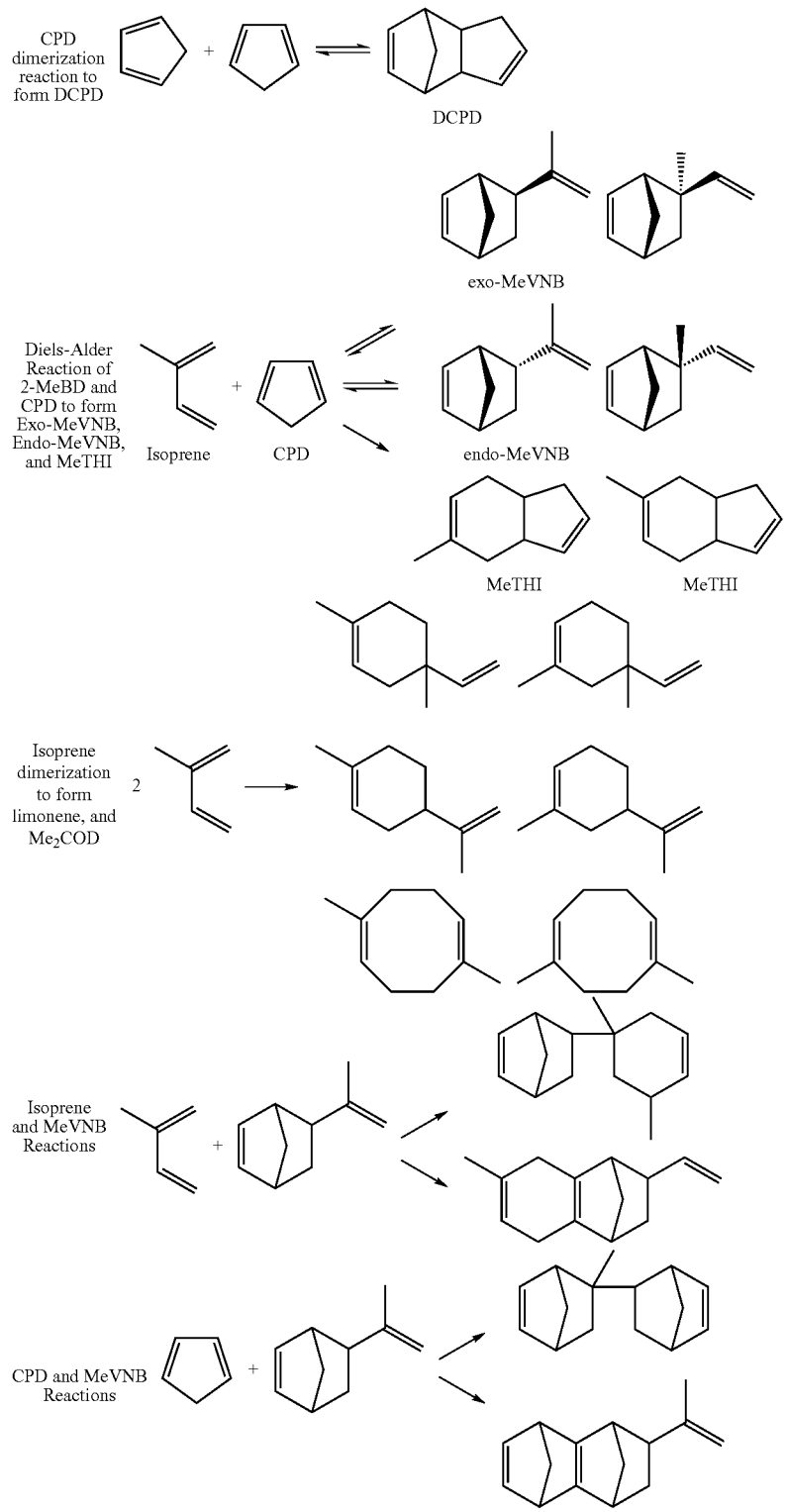

SCHEMES 2

It should be noted that while it is generally advantageous to use an exo-/endo-alkenylnorbornene mixture that has a purity of at least 99% by weight as a starting material for embodiments of the present invention, as such embodiments reduce or eliminate the effects of typically found impurities on the yield and purity of the final product, other less pure grades of such a starting mixture, for example 90% by weight, can also be employed. That being said, some embodiments of the present invention encompass a distillation prior to beginning the Cope Rearrangement reaction to reduce the concentration of some impurities, for example, where the starting mixture is a VNB mixture, the impurities can encompass 1,3-COD, 1,5-COD, ethylnorbornene, ethylidene norbornene, 5,6-dimethylnorbornene and VCH, among others.

With regard to producing an exo-ANB of high purity, it is well known that ANB mixtures formed via a Diels-Alder pathway will have a specific ratio of exo-ANB to endo-ANB that is a function of the starting materials and reaction conditions. For example, many commercially available VNB-mixtures have an exo-/endo-ratio of about 1:3. However, as other ANBs can have other ratios, and as such other ANBs can be provided via other reaction pathways, embodiments in accordance with the present invention encompass ANB isomer mixtures having exo-/endo-isomer ratios as high as 99 to 1 and as low as 1:99.

Embodiments of the invention can include methods of producing high purity exo-ANB from a endo-/exo-ANB mixture by controlling the vapor pressure of such mixture in an open system so that 1) endo-ANB is selectively converted into tetrahydroindene, methyltetrahydroindene, or another tetrahydroindene compound corresponding to such endo-ANB (collectively referred to as Cope rearrangement reaction products) and 2) decomposition products having a boiling point lower than that of the endo-/exo-ANB (lights) are released from the endo-/exo-ANB mixture contained within the open system. The vapor pressure is controlled by applying an effective amount of heat (an amount of heat effective to cause a Cope Rearrangement of the endo-ANB) at a first pressure and subsequently controlling one or both of the temperature and pressure to minimize the formation of lights from exo-ANB while allowing the Cope Rearrangement to continue. Since at least one of heat and pressure is applied to the endo-/exo-ANB mixture in an open system, lights can be released from the system, contrary to a sealed or closed system where lights can co-react to form undesired components.

In this context, an open system is an unsealed system, that is to say it is open to a source of reduced pressure relative to the system pressure. An open system permits the release of components therefrom, such as through boiling, evaporation, or other vaporization means. While application of heat and/or pressure can be initially applied to a closed system, as long as the system is opened to subsequently allow for the release of lights, the system is considered open in accordance with embodiments of the present invention.

As lights are released from the endo-/exo-ANB mixture, and as the THI or other Cope rearrangement reaction product is formed, the identity of the mixture (the identity and the amount of each component in the mixture) changes compared to the initial endo-/exo-ANB mixture to which heat and/or pressure was applied. Consequently, in such a dynamic environment, the amount of heat and/or pressure applied to control or maintain a desired vapor pressure and vaporization rate can constantly change. The vapor rate is controlled to affect a desired balance between the rate at which endo-ANB disappears, primarily through its conversion to a Cope rearrangement reaction product such as THI via the Cope Rearrangement, and the rate at which exo-ANB disappears, primarily through its decomposition via a reverse Diels-Alder reaction. Additionally such control is effective to allow the release of lights from the reaction system to reduce or eliminate the formation of undesirable components formed via the co-reaction of such lights.

With regard to performing the controlled Cope Rearrangement encompassed by embodiments of the present invention, such can be performed in a number of ways and be in accordance with the basic principles of such embodiments. Thus, some such embodiments of the present reaction are performed in a batch manner while others are performed in a semi-batch manner and still others in a continuous manner. Further still, some embodiments are performed in a manner that encompasses a combination of such batch, semi-batch and continuous processes. For example, a continuous process embodiment can be performed in an autoclave intended for continuous operation, a tube or loop reactor, or a multistage continuous reactor train with any combination of two or more of these reactors in series.

In an exemplary semi-batch process, an ANB mixture is added as a function of time, such function related to the loss of lighter decomposition components from the system. Thus, as lights are released from the reactor, additional amounts of the initial ANB mixture can be introduced into the reactor incrementally to maintain a relatively constant reactor volume for as long as practical. Advantageously, it has been found that the rate of product generation (reaction rate) is enhanced for these incremental additions by, it is believed, the presence of, for example, already generated THI where the ANB is VNB.

Still further to how embodiments in accordance with the present invention can be performed, such can be an isobaric process, that is to say at a constant pressure, an isothermal process, that is to say at a constant temperature, or such can be a process where both temperature and pressure are varied. For isobaric embodiments an initial temperature is selected that is appropriate for the set pressure that will be maintained. Subsequently, the temperature is varied as required to maintain the isobaric condition. Thus, pressure is constant ($P_{initial}=P_{final}$) and temperature is varied such that Tinitial is changed as needed to effectively remove light components and to increase the rate of reaction of the endo-ANB. For such isobaric embodiments, control of the temperature can be by any appropriate method including, but not limited to, linear or stepped ramp protocols.

For isothermal embodiments an initial pressure is selected that is appropriate for the set temperature that will be maintained. Subsequently, the pressure is varied as required to maintain the isothermal condition. Thus, temperature is constant ($T_{initial}=T_{final}$) and pressure is varied such that $P_{initial}$ is changed as needed to effectively remove light components and to increase the rate of reaction of the endo-ANB. For such isothermal embodiments, control of the pressure can be by any appropriate method including, but not limited to, linear or stepped ramp protocols. For some isothermal embodiments, a reactor pressure greater than atmospheric pressure is selected initially ($P_{initial}>P_{Atmospheric}$) to elevate the boiling point (temperature at which liquid vapor pressure equals that of atmospheric pressure) of the starting reaction liquid composition above its atmospheric boiling point and then the pressure is lowered ($P_{final}<P_{initial}$) as the reaction proceeds to allow for the removal of higher boiling point light components as they are generated. For such isothermal embodiments, control of the pressure can be by any appropriate method including, but not limited to, linear or stepped ramp protocols.

Some embodiments of the present invention allow for both the temperature and pressure of the reaction system to be varied. Thus, for some embodiments a linear or stepped temperature and/or pressure ramp is employed in a batch or semi-batch process, while for other embodiments a temperature and/or pressure profile is arranged in a multi-reactor continuous process.

Generally, control of temperature and/or pressure is accomplished by one or more devices that can measure or sense one or both of temperature and pressure and one or more devices that can effect a change in temperature and/or pressure. In some embodiments, a single device or means is provided to accomplish the measuring and controlling. For example where both temperature and pressure can vary, such a scheme could have a continuous temperature sensing device that provides either the sensed temperature or a calculated rate of temperature change, coupled to a device capable of changing the reaction pressure and or temperature in an appropriate manner. Alternatively, pressure can be continuously monitored. For isobaric or isothermal embodiments in accordance with the present invention, separate or combined sensing and control devices can maintain one of the pressure or temperature constant while appropriately varying the other to maintain a desired rate of reaction. Thus it will be understood that a device that both senses and controls reaction temperature and/or pressure is within the scope and spirit of the present invention.

Regardless of whether an embodiment is isobaric, isothermal or one where both pressure and temperature are varied, generally, the reaction temperature used is within the range of 100° C. to 250° C. In some embodiments it is in the range from 140 to 190° C., and in yet other embodiments such range is from 145 to 165° C. While any of the aforementioned temperature ranges are effective, it should be noted that at lower temperatures the decomposition of an exo-ANB is slower than at higher temperatures. While this can be advantageous, it should also be noted that the rate of rearrangement of the endo-ANB to the corresponding Cope rearrangement product is also slower thus increasing the amount of time needed to maximize the yield of exo-ANB. It should also be noted that by defining the above temperature ranges, it is not implied that a single temperature from one of such ranges need be selected, rather, one or more temperatures can be utilized to maximize yield and minimize reaction time. For example, it has been found that the use of high temperature at the beginning of the reaction makes it possible to reduce synthesis times while the use of lower temperature at the end of the reaction ensures conservation of the exo-ANB content in the mixture. Thus, for reactions employing a low initial concentration ratio of exo-ANB to endo-ANB (e.g. 1:3) an initial reaction temperature of 160° C. or higher is generally advantageous, and as the reaction proceeds and such ratio increases to about 1:1 or higher, it is generally advantageous to reduce the reaction temperature to a lowest acceptable temperature. That is to say to a temperature where the Cope Rearrangement reaction can still proceed but where decomposition of either exo or endo-ANB is greatly reduced, for example a temperature of 145° C. or less. In this manner it has been found that extremely low to non-detectable levels of endo-ANB may be obtained whilst maintaining a high rate of recovery for exo-ANB.

It should also be noted that when the reaction temperature exceeds about 190° C., undesirable rapid decomposition of both exo-ANB and endo-ANB, isomerization, or polymerization of the starting ANB-mixture and unacceptable loss of the product may occur, thus reducing yield. In general, where an embodiment in accordance with the present invention includes selecting a specific temperature or temperature range, such a selection will control the rates of reaction and dictate selection of an appropriate pressure or pressures that will ensure the effective removal of light components and thus maximize the yield of the exo-ANB product.

Thus, for embodiments in accordance with the present invention, the presence of components that are higher in boiling point than the specific exo-ANB selected, while retained in the reaction mixture, appear to have little or no impact on the yield of such exo-ANB. As seen in the Gas Chromatography (GC) retention times shown below, it should be evident that such higher boiling point products (for example those products having a boiling point equal to or higher than that of THI or MeTHI) are efficiently separated from desired product via distillation or other separation methods. Advantageously it has been found that such embodiments do not form any significant by-products having boiling points at or near to that of exo-VNB (e.g. VCH) or exo-MeVNB (e.g. DCPD or limonene) thus making the separation of these isomers, as well as other exo-ANB isomers, from any contained by-products routine.

In some embodiments of the present invention, other components are added to the reaction mass, for example other organic compounds or solvents. Such other components may be used singly or in admixture of two or more and should be unreactive to both the ANB and any reaction products that may be formed during the thermolysis. Further, such components should not be susceptible to decomposition or polymerization under the reaction conditions. Generally, such other components are liquids at room temperature and have a boiling point higher than the selected ANB. In this manner such components can be readily separated from the reaction mixture to provide exo-ANB in high yield and quality. Exemplary other components include, but are not limited to, hydrocarbons having 10 or more carbon atoms, carboxylic esters, halohydrocarbons, nitriles, and aldehydes. It should be noted that the addition of such other components can be advantageous for aiding in the control of reaction temperatures and pressures and composition of the reaction mass where the purity of such components is sufficiently high that no impurities are added that would impact the purity or yield of the exo-ANB.

Exemplary hydrocarbons having 10 or more carbon atoms include, but are not limited to, n-decane (boiling point (bp) 174° C.), undecane (bp 196° C.), cis-decahydronaphthalene (cis-decalin) (bp 196° C.), trans-decahydronaphthalene (trans-decalin) (bp 187° C.), tetrahydronaphthalene (tetralin) (bp 208° C.), n-dodecane (bp 216° C.), hexadecane (bp 288° C.), eicosane (bp 343° C.), p-cymene (bp 177° C.), n-butylbenzene (bp 183° C.), dodecylbenzene (bp 331° C.), mesitylene (bp 165° C.), 1,3-diethylbenzene (bp 181° C.), n-butylcyclohexane (bp 181° C.), n-pentylcyclopentane (bp 181° C.), 1-pentylnaphthalene (bp 306° C.), nonylcyclohexane (bp 282° C.), n-decylcyclopentane (bp 278° C.), 2-methyltetradecane (bp 265° C.), and those kerosenes and light oils which have a boiling point of 150° C. or higher, preferably 180° C. or higher.

Exemplary carboxylic esters are cyclohexyl acetate (bp 174° C.), 2-ethylhexyl acetate (bp 197° C.), and isopentyl butyrate (bp 185° C.); exemplary halogenated hydrocarbons are α-chloronaphthalene (bp 259° C.), bromobenzene (bp 155° C.), 1,2-dichlorobenzene (bp 180° C.), and α-bromonaphthalene (bp 281° C.); exemplary nitrites are heptanenitrile (bp 187° C.), octanenitrile (bp 204° C.), benzonitrile (bp 191° C.), and benzyl cyanide (bp 233° C.); and exemplary aldehydes are benzaldehyde (bp 179° C.) and salicylaldehyde (bp 197° C.). It should be noted that while specific materials are exemplified above, such does not limit the scope and spirit of the embodiments of the present application, but rather provides for a better understanding of such embodiments.

Alternatively, for some embodiments of the present invention, both temperature and pressure are altered consecutively or concurrently. That is to say one or both of the temperature and pressure are varied to predetermined set points, In one such embodiment, the temperature of the reactor can be set at temperature ($T_{initial}$) where the reaction proceeds rapidly and the pressure ($P_{initial}$) is set to permit the release of lights in a controlled manner, then subsequently both temperature ($T_{final} \neq T_{initial}$) and pressure ($P_{final} \neq P_{initial}$) are changed, either consecutively or concurrently, in an appropriate manner until essentially all of the endo-ANB isomer has been converted to its appropriate THI derivative product.

For some embodiments in accordance with the present invention, it has been found to be advantageous to set $P_{initial}$ of the system to at or slightly above the vapor pressure of the reaction mixture thus permitting removal of lights, while maintaining the temperature of the reaction mixture at or below its boiling point. After essentially all of such lights are removed, generally both pressure and temperature are modified in an appropriate manner to ensure that the reaction occurs at the requisite rate with retention of the desired exo-ANB. For example, an initial endo/exo-VNB mixture having its temperature varied over the range of from about 100 to 250° C., would have a range of pressure of about 4.5 psia (pounds per square inch absolute) to 125 psia. If the temperature of such mixture was varied from about 140° C. to 190° C., the pressure would be varied from about 14 psia to 45 psia and where temperature is varied from about 145° C. to 165° C., the appropriate range of pressure would be from about 16 psia to 26 psia.

In some embodiments, an ANB-mixture may be heated, initially, to its boiling point at a first pressure, thus causing the mixture to be at a first reflux rate with venting. Then as such pressure is changed to a second pressure, the temperature is adjusted to maintain the reaction mixture at the first reflux rate as the Cope Rearrangement reaction proceeds.

In other embodiments the vent stream of the reaction system is passed through a fractional distillation column to precisely control the composition of the vented gas in contrast to the embodiments described immediately above. Advantageously, the use of such fractional distillation column will more effectively separate light components from exo-ANB than where such a column is not used.

It should be noted that the total time the ANB mixture is heated to a temperature sufficient to begin the Cope Rearrangement reaction has an effect on the quality of the end product. Thus, the selection of an appropriate initial temperature and/or pressure, for embodiments in accordance with the present invention, as well as whether such embodiments are isobaric, isothermal or encompass controlled variation of both temperature and pressure, is made with consideration for the relationship between the relative rates for the disappearance of endo-ANB (via the Cope Rearrangement and/or via a reverse-Diels-Alder reaction) and the disappearance of exo-ANB (via a reverse-Diels-Alder reaction). Thus, while the absolute yield of exo-ANB can be maximized where the temperature employed is kept low and the reaction allowed to continue for an extended time, the conversion of endo-ANB to appropriate THI derivative (as well as the loss of exo-ANB via a reverse Diels-Alder reaction) is enhanced at higher temperatures. It is believed that a reaction time from about 48 hours to about 580 hours within a temperature range from about 145° C. to 165° C. is advantageous for both yield and quality.

It should be noted that regardless of which of the several embodiments in accordance with the present invention is employed, it is advantageous to maintain the rate of disappearance of endo-ANB (kendo) relative to the rate of disappearance of exo-ANB ($k_{exo}$) also referred to as the $k_{endo}/k_{exo}$ ratio, at a value as high as possible. For example, it has been found that where such ratio is at or above 20 a desirable yield and quality of exo-ANB is readily obtained.

In other embodiments in accordance with the present invention, an inert gas can be swept through the headspace of the reactor vessel and/or sparged through the reaction liquid mixture. The inert gas may be selected from any non-reactive gas such as helium, nitrogen, argon or the like and where employed, has been found to assist in the removal of lights from the reaction mixture.

Additionally, it has been found that the addition to the reaction mixture of an antioxidant, for example butylated hydroxytoluene (BHT) or 4-tert-butylcatechol (TBC), can be advantageous. Such antioxidant can be added either initially, or at other stages subsequent to the initiation of the Cope Rearrangement reaction serving to reduce or eliminate any undesirable thermo-oxidative decomposition.

Advantageously, essentially pure exo-ANB can be obtained from the thermolyzed reaction mixture via fractional distillation or alternately a mixture of exo-ANB, THI derivative, and a small amount of "heavies" can be obtained by partially distilling the reaction mixture followed by a more rigorous distillation to yield exo-ANB and the appropriate THI derivative separately in high purity.

Embodiments in accordance with the present invention encompass processes for the formation of essentially pure exo-alkenylnorbornenes. It should be noted, however, that embodiments of the present invention are not limited to the vinylnorbornene and methyl-vinylnorbornene isomers shown in Schemes 1 and 2, respectively. Rather such alkenylnorbornenes are believed to be representative of any other alkenylnorbornene represented by one of structural formulae I and II shown below. Thus, the scope and spirit of the present invention extend to such structural analogs of VNB and MeVNB.

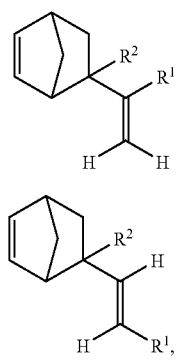

where $R^1$ may be selected from a $C_1$ to $C_{10}$ alkyl group, or where the number of carbons is sufficient a branched or cyclic alkyl group, or $C_1$ to $C_{10}$ linear alkyl substituted phenyl group; and where $R^2$ may be selected from H or Me. More specifically, alkenylnorbornenes in accordance with embodiments of the present invention may be selected from 2-(1-propenyl)-5-norbornene, isopropenyl-2-norbornene, 5-(1-methylenepropyl)norbornene, 5-(2-methyl-1-methylenepropyl)norbornene, or 5-(1-phenylethenyl) norbornene. As one of ordinary skill in the art will recognize, such structures and exemplary materials provide alkenylnorbornenes having an endo-isomer capable of undergoing a thermal Cope Rearrangement reaction.

With respect to any figure or numerical range for a given characteristic, a figure or a parameter from one range may be combined with another figure or a parameter from a different range for the same characteristic to generate a numerical range.

EXAMPLES

The following examples are provided to be illustrative only and therefore are in no way restrictive to the scope and spirit of the present invention.

In the various examples that follow, where gas chromatography (GC) methods were used to follow the progress of the reactions described and/or to analyze the purity of a final composition, the following column and temperature program was used. Further the retention times provided were representative of those obtained: a 60 meter, 0.25 mm ID SBP-Octyl (Supelco) Column having a 0.25 μm film; after injection of the sample at an injector temperature of 200° C., the column temperature was ramped from 50° C. to 150° C. @ 5° C./min., and then to 250° C. @ 40° C./min. and held at that temperature for 5 min.; a Flame Ionization Detector (FID) heated to 250° C. was used to detect the eluted materials. Retention times for a VNB based reaction were, BD: 5.8 min; CPD: 6.4 min; VCH: 12 min; endo-VNB: 13.6 min; exo-VNB: 13.6 min; THI: 16.7 min; DCPD: 18.4 min; and Heavies 1: 23-26 min. For a MeVNB based reaction the retention times were, IP: 6.4 min; CPD: 6.6 min; exo-MeVNB: 17.5 min; endo-MeVNB: 17.6 min; DCPD: 18.6 min; Limonene: 19 min; MeTHI: 19.3 min; and Heavies: 24-28 min.

For all synthetic and thermolysis examples shown below, charged liquid materials were sparged with nitrogen to remove dissolved oxygen and moisture. In addition, all reaction vessels employed were purged with nitrogen to remove any oxygen from the vessel head-space.

Comparative Example

Thermolysis of Exo-Endo-VNB Employing High Pressure Reaction Conditions

A sample of high purity Nisseki endo-/exo-VNB was heated for 40 minutes in a Buchi LIMBO reactor at 206° C. at a pressure of 200 psia to duplicate the conditions described generally in J. Chem. Soc. Perkin Trans, 1, 1991, 1981-1991, L. Crombie and K. M. Mistry. GC analysis of the starting VNB mixture was 0% BD, 0% CPD, 0.2% VCH, 81.5% endo-VNB, and 18.2% exo-VNB, 0.1% THI and 0% heavies. After the experiment was completed, the reaction mixture contained 1.4% BD, 0.3% CPD, 0.8% VCH, 6.6% endo-VNB, and 14.6% exo-VNB, 55.3% THI and 21.1% heavies. Thus, the VCH content versus the contained exo-VNB increased from 0.2% to 0.8% during the course of the experiment and this corresponds to a final 4.8% VCH in contained exo-VNB. The conversion of endo-VNB to THI was incomplete. Additionally, the high temperature caused the formation of 21.1% heavies. Thus, in contrast to the literature evidence, no readily recoverable high purity exo-VNB is generated under these reaction conditions.

Examples 1-8

Thermolysis of Commercially Available Endo-/Exo-Vinylnorbornene

In an experiment analogous to that of the Comparative Example but at a lower temperature, thermolysis of samples of four commercially available VNB isomeric mixtures was performed as described below.

Example 1-4

Four endo-/exo-vinyinorbornene samples were obtained from commercial sources Acros (Acros Organics), Aldrich (Sigma-Aldrich Co.), Nisseki (Nisseki Chemical Texas Inc.), and TCI (TCI America). A 1 mL sample of each material was placed into a HiP MS micro reactor (High Pressure Equipment Company, Erie, Pa., USA) and heated to 180° C. for 26 hours. The samples were then cooled and the contents of each micro reactor analyzed by GC versus their starting composition. Analysis is shown in Table 1.

Examples 5-8

A sample of endo-/exo-vinylnorbornene was obtained from INEOS (INEOS Belgium NV). A 1 mL sample was placed into a HiP MS micro reactor and heated to 180° C. for 26 hours. A control sample of Nisseki endo-/exo-VNB was employed under the sample reaction conditions. The samples were then cooled and the contents of each micro reactor analyzed by GC versus their starting composition. Analysis is shown in Table 2.

TABLE 1

Thermolysis of Commercial Endo-/Exo-VNB Materials

Examples 1, 2, 3 and 4

(GC % Area)

| Ex # | VNB MFG | BD | CPD | VCH | Endo-VNB | Exo-VNB | THI | Heavies | VCH (%) in Exo-VNB |
|---|---|---|---|---|---|---|---|---|---|
| 1 | Acros-Initial | 0 | 0 | 0 | 71.19 | 26.27 | 0.11 | 2.43 | 0.00% |
| 1 | Acros-Final | 0.5 | 0.09 | 0.22 | 2.08 | 19.18 | 52.74 | 25.19 | 1.12% |
| 2 | Aldrich-Initial | 0 | 0 | 0.05 | 81.54 | 18.41 | 0 | 0 | 0.25% |
| 2 | Aldrich-Final | 0.52 | 0.07 | 0.29 | 1.59 | 12.32 | 59.97 | 25.23 | 2.27% |
| 3 | TCI-Initial | 0 | 0 | 0.04 | 80.18 | 18.05 | 0 | 1.73 | 0.22% |
| 3 | TCI-Final | 0.5 | 0.07 | 0.32 | 1.29 | 12.84 | 63.02 | 21.97 | 2.42% |
| 4 | Nessiki-Initial | 0 | 0 | 0.24 | 81.54 | 18.14 | 0.08 | 0 | 1.31% |
| 4 | Nessiki-Final | 0.6 | 0.09 | 0.43 | 3.29 | 13.51 | 58.84 | 23.29 | 3.11% |

TABLE 2

Thermolysis of Commercial Endo/Exo-VNB Materials
Examples 5, 6, 7 and 8
(GC % Area)

| Ex # | VNB MFG | BD | CPD | VCH | Endo-VNB | Exo-VNB | THI | Heavies | VCH (%) in Exo-VNB |
|---|---|---|---|---|---|---|---|---|---|
| 5 | Ineos 1-Initial | 0 | 0 | 0.06 | 73.91 | 25.99 | 0.05 | 0 | 0.21% |
| 5 | Ineos 1-Final | 0.39 | 0.08 | 0.27 | 3.59 | 20.82 | 54.03 | 20.83 | 1.28% |
| 6 | Ineos 2-Initial | 0 | 0 | 0.06 | 74 | 25.72 | 0.05 | 0.18 | 0.22% |
| 6 | Ineos 2-Final | 0.41 | 0.08 | 0.26 | 3.93 | 21.06 | 53.86 | 20.4 | 1.24% |
| 7 | Nessiki 1-Initial | 0 | 0 | 0.24 | 81.54 | 18.14 | 0.08 | 0 | 1.31% |
| 7 | Nessiki 1-Final | 0.37 | 0.06 | 0.54 | 1.05 | 12.4 | 60.46 | 25.12 | 4.15% |
| 8 | Nessiki 2-Initial | 0 | 0 | 0.24 | 81.76 | 17.79 | 0.08 | 0.13 | 1.32% |
| 8 | Nessiki 2-Final | 0.41 | 0.07 | 0.47 | 3.13 | 13.66 | 58.46 | 23.8 | 3.35% |

As shown in Tables 1 and 2: (i) the duplicate Nisseki sample runs were essentially equivalent (see, Ex 4, 7 and 8); (ii) not all commercial samples are of the same composition; (iii) each experiment showed the formation of BD and CPD, a significant increase in the amount of "heavies" and either the formation of VCH or an increase in VCH concentration. These observations are consistent with the results of the comparative example and suggest that the sealed tubes retain the reverse-Diels-Alder products of BD and CPD which can then form the VCH that is found as well as the heavier components at the reaction temperature employed. Thus it is readily seen that previously reported sealed thermolysis methods result in an exo-VNB product free from or even essentially free from VCH, thus making the isolation of high-purity exo-VNB, and by inference high-purity exo-ANBs very difficult if not impossible.

Example 9

Thermolysis of Endo-/Exo-Vinylnorbornene Mixture

Under a nitrogen atmosphere, endo-/exo-VNB (Acros) (1262 g) was added to a 3000 mL three-necked glass flask fitted with a glass air-cooled column (12 inch height) filled with Pro-Pak® stainless steel packing and vented to an oil bubbler. The endo-/exo-VNB mixture was initially heated until a 4 inch head of vapor was observed in the packed column. The initial pot temperature was about 141° C. In this case, the packed column was increasing the normal boiling point of the mixture, i.e., atmospheric boiling point of the liquid was raised by the back-pressure exerted from the packed column of condensing vapors. During the course of the experiment, a period of approximately nine days, the temperature of the reaction mixture was raised incrementally so that the same 4 inch vapor height was maintained in the packed column. The details of the experiment are noted in Table 3.

After heating for a total of 200 hours, the reaction liquid temperature was at 165° C. The weight of the final mixture was 1176 g (93% recovery) indicating a loss of 86 g of by-products. The final reaction mixture was analyzed by GC and determined to have the following ratio of components: 0.01% VCH, 0.1% endo-VNB, 23.5% exo-VNB, 74% THI, and 8.6% heavies and very low levels of BD and CPD were detected in the sample. The final ratio of exo-VNB to VCH was 99.9% to 0.1% and exo-VNB was recovered in 84.9% yield. While some VCH was formed during the course of this reaction (See, Example 1 for the initial concentration of VCH in Arcos VNB and for its concentration after a 26 hour sealed thermolysis—Table 1) compared to the results of Examples 1-8, the results obtained here, where the reaction vessel allowed "lights" to exit, indicate that under the controlled pressure or vented conditions of this experiment, essentially all the BD and CPD was able to leave the reactor system before any significant amount of the undesirable VCH by-product was formed.

In this example the use of a fractionation column was demonstrated because the boiling reaction mixture was under reflux through a packed column containing Pro-Pak® packing and the only components detected in the column vent stream were BD and CPD.

The final reaction material was distilled (see Table 3 for distillation details) using a 12 inch Pro-pak® column at a reduced pressure of 200-300 mTorr, overhead temperature of 21° C. to yield three cuts of a >99% pure exo-VNB/THI mixture (34.5% exo-VNB and 64.6% THI) with undetectable levels of VCH and endo-VNB by GC analysis. This example shows that a pure exo-VNB/THI mixture can be synthesized and recovered easily. When some fractionation occurs the exo-VNB content is increased in the samples.

TABLE 3

Isobaric Thermolysis of Exo/Endo-VNB (Acros)
Example 9: Thermolysis Details

GC Analysis (Area % and Retention Times in Minutes)

| | GC RT (min) | | | | | | | | |
|---|---|---|---|---|---|---|---|---|---|
| Time (day) | 5.76 | 5.93 | 6.38 | VCH 12.04 | 12.67 | endo-VNB 13.44 | exo-VNB 13.58 | 13.75 | 14.06 |
| 0 | 0.00 | 0.00 | 0.00 | 0.01 | 0.01 | 71.48 | 27.71 | 0.01 | 0.02 |
| 7 | 0.00 | 0.01 | 0.01 | 0.01 | 0.01 | 0.84 | 26.25 | 0.01 | 0.00 |
| 8 | 0.01 | 0.01 | 0.03 | 0.01 | 0.01 | 0.26 | 24.84 | 0.01 | 0.00 |

TABLE 3-continued

Isobaric Thermolysis of Exo/Endo-VNB (Acros)
Example 9: Thermolysis Details

| 9 | 0.02 | 0.00 | 0.05 | 0.01 | 0.01 | 0.06 | 23.52 | 0.01 | 0.00 |
|---|---|---|---|---|---|---|---|---|---|
| Mixture | | | | 0.01% | | 0.06% | 23.70% | | |
| VCH: exo-VNB | | | 0.06% | | | | 99.94% | | |

GC Analysis (Area % and Retention Times in Minutes)

| Time (day) | 14.11 | 14.18 | 14.33 | 14.53 | 14.76 | 15.21 | 16.36 | THI 16.72 | Heavies |
|---|---|---|---|---|---|---|---|---|---|
| 0 | 0.34 | 0.07 | 0.10 | 0.03 | 0.00 | 0.12 | 0.00 | 0.11 | 0.00 |
| 7 | 0.35 | 0.00 | 0.11 | 0.01 | 0.01 | 0.14 | 0.02 | 65.40 | 6.82 |
| 8 | 0.35 | 0.00 | 0.11 | 0.01 | 0.01 | 0.14 | 0.02 | 66.17 | 8.01 |
| 9 | 0.36 | 0.00 | 0.11 | 0.01 | 0.02 | 0.14 | 0.03 | 66.99 | 8.65 |
| Mixture | | | | | | | | 67.51% | 8.72% |
| VCH: exo-VNB | | | | | | | | | |

Distillation Details

| | Mass (gm) | Weight (%) | Pot Temp (° C.) | Vapor Temp (° C.) | Pres (mTorr) | exo-VNB (%) | THI (%) |
|---|---|---|---|---|---|---|---|
| Initial Charge | 1262.0 | | | | | | |
| Losses During Thermolysis | 251.8 | −19.95% | | | | | |
| Distillation Charge | 1010.3 | | | | | | |
| Distillation Cut 1 | 286.9 | 22.73% | 37 | 21 | 200 | 34.52 | 64.57 |
| Distillation Cut 2 | 365.4 | 28.95% | 37 | 21 | 300 | 24.63 | 74.54 |
| Distillation Cut 3 | 213.5 | 16.92% | 64 | 21 | 300 | 6.23 | 93.13 |
| Still Bottoms | 144.5 | 11.45% | | | | | |
| Recovered Total | 1010.3 | | | | | | |
| Product Cuts | | 68.61% | | | | | |

Example 10

Thermolysis of Endo-/Exo-Vinylnorbornene:THI (50:50) Mixture

Reaction conditions analogous to those of Example 9 were employed except that THI was initially added to the reaction pot to allow for a higher boiling point temperature to be employed. Specifically, 50 g of endo-/exo-VNB (Aldrich) and 50 g of THI (Promerus) were charged to a 250 mL flask fitted with a column filled with stainless steel packing, a water cooled condenser and an oil bubbler. The charged liquid was heated in an oil bath set at 170° C. When gentle boiling of the liquid was observed, the pot temperature was 157° C. After 24 hours of being heated by the oil bath, the pot temperature was 158° C. and after 90 hours it had increased to 165° C. At this point heating was stopped and the mixture was allowed to cool. The weight of the final mixture was 94.8 grams and its composition was 13.5% exo-VNB (GC/NMR analysis) and 86.5% THI. No BD, CPD, or VCH were detected in the sample.

Since this thermolysis was run in an open to atmosphere reaction vessel, as the reaction proceeded all the lights were able to leave the system. Additionally the endo-VNB was converted to THI thus the composition of the reaction mixture changed to be one of higher THI content. As this change occurred and since the pot was being heated by a source set to a temperature slightly above the mixture's initial boiling point, the observed pot temperature increased. Further as any lights that formed via reverse Diels-Alder reactions were vented, they could not combine to form VCH or other undesirable by-products. Of note here is that the use of an admixture of endo-/exo-VNB with a high boiling point liquid such as THI allowed for a higher initial temperature to be obtained resulting in an acceleration of the reaction rate of the Cope Rearrangement.

Example 11

Thermolysis of Endo-/Exo-Vinylnorbornene (Nisseki) in a Sealed Reactor

To obtain reaction kinetic data, a thermolysis reaction analogous to that of Example 9, but where the reaction vessel was sealed, was performed. Specifically, a sample of endo-/exo-VNB (Nisseki) was charged to a Buchi LIMBO reactor (max. pressure of 50 psig) and heated to 180° C. The reactor was maintained at that temperature for 28 hours being allowed to build its own internal pressure.

The reaction mixture was cooled to room temperature and its composition determined to allow the reaction rate constant (based on a first order kinetic model) to be calculated. The rate of disappearance of exo-VNB was found to be $9.98E-06$ $s^{-1}$ and for endo-VNB, $7.8E-05$ $s^{-1}$. Thus, while both species are disappearing, it is believed that the rearrangement of endo-VNB (Cope rearrangement) provides for its disappearance being at a rate 7.8 times faster than the disappearance of exo-VNB, where such disappearance is likely limited to a decomposition pathway.

In addition, it was observed that the vinylcyclohexene content versus the contained exo-VNB content increased from 1.3% to 10.8%. In contrast to the literature evidence, no high purity exo-VNB is generated under these conditions. Thus, there is no reduction in VCH content performing the reaction at 50 psig to 200 psig (see Comparative Example 3).

Example 12

Thermolysis of Commercially Available Endo-Exo-Vinylnorbornene Under Back-Pressure Control

Isothermal Reaction

For each of the three Runs in this example, the quantity of endo-/exo-vinyl norbornene (≥99% VNB Nisseki Chemical) indicated was charged into a reactor system consisting of the following major equipment: jacketed/agitated reactor, dual overhead condensers, and overhead condensate receiver tank. Initially, the endo-/exo-VNB mixture was heated to the target temperature and pressure was adjusted until the reactor liquid was observed to be gently boiling. The mixture was maintained at the target temperature and pressure was incrementally adjusted to maintain this gentle boiling condition. Details of the isothermal target temperatures and ramped pressure conditions for each run are given in the tables below. The initial ratio of VNB exo/endo isomers was 81.45% endo-VNB to 18.22% exo-VNB with 0.24% VCH, and 0.08% THI also found present.

Run 1
Reactor Charge: VNB 40.5 kg
Reactor Discharge: 28.0 kg
Overhead Condensate Collected: 10.9 kg Reactor Vent Losses: 1.6 kg
Isothermal Reaction Temperature: 180° C.
Reaction Time: 24 hours
Reaction Pressure: Start 30 psig/End 24 psig
Composition of the reaction mass expressed as
GC area % at various reaction times.
The "0" hour was time when reactor reached the target temperature.

|  | \multicolumn{7}{c}{Time (hours)} |
| --- | --- | --- | --- | --- | --- | --- | --- |
|  | 0 | 4 | 8 | 12 | 16 | 20 | 24 |
| Reactor Pressure (psig) | 30.0 | 30.0 | 28.5 | 26.9 | 25.8 | 25.0 | 24.2 |
| endo-Vinylnorbornene | 53.49 | 19.88 | 13.00 | 7.12 | 0.23 | 0.09 | 0.07 |
| exo-Vinylnorbornene | 14.41 | 15.00 | 15.43 | 11.67 | 6.84 | 5.78 | 4.97 |
| Tetrahydroindene | 8.46 | 40.99 | 52.35 | 51.11 | 58.26 | 60.64 | 57.97 |
| Vinylcyclohexene | 0.17 | 0.25 | 0.32 | 0.37 | 0.54 | 0.60 | 0.58 |
| Butadiene | 0.12 | 0.39 | 0.44 | 0.39 | 0.25 | 0.24 | 0.21 |
| Cyclopentadiene | 0.21 | 0.25 | 0.21 | 0.12 | 0.06 | 0.05 | 0.04 |
| Heavies | 23.14 | 23.24 | 18.24 | 29.22 | 33.81 | 32.60 | 36.14 |
| exo-VNB/Total VNB (%) | 21.2 | 43.0 | 54.3 | 62.1 | 96.8 | 98.5 | 98.6 |

Run 2
Feed VNB 50 kg
Product 44.1 kg
Condensate 5.2 kg
Reaction Temperature 180° C.
Reaction Time 17 hours
Reaction Pressure Start 28 psig/End 21 psig
Composition of the reaction mass expressed as
GC area % at various reaction times.
The "0" hour was time when reactor reached the target temperature.

|  | Time (hours) | | | | | | |
| --- | --- | --- | --- | --- | --- | --- | --- |
|  | 0 | 4 | 8 | 12 | 14 | 16 | 17 |
| Reactor Pressure (psig) | 28.0 | 28.0 | 25.6 | 23.6 | 22.6 | 21.6 | 21.1 |
| endo-Vinylnorbornene | 69.15 | 42.72 | 1.09 | 0.16 | 0.11 | 0.14 | 0.49 |
| exo-Vinylnorbornene | 18.25 | 16.05 | 10.46 | 8.96 | 8.17 | 6.74 | 6.83 |
| Tetrahydroindene | 9.95 | 24.28 | 58.58 | 63.46 | 62.80 | 60.40 | 62.87 |
| Vinylcyclohexene | 0.25 | 0.24 | 0.40 | 0.49 | 0.50 | 0.50 | 0.53 |
| Butadiene | 0.23 | 0.30 | 0.38 | 0.31 | 0.29 | 0.22 | 0.23 |
| Cyclopentadiene | 0.32 | 0.28 | 0.08 | 0.07 | 0.06 | 0.05 | 0.06 |
| Heavies | 1.85 | 16.12 | 29.01 | 26.55 | 28.07 | 31.94 | 29.00 |
| exo-VNB/Total VNB (%) | 20.9 | 27.3 | 90.6 | 98.3 | 98.7 | 98.0 | 93.3 |

Run 3
Feed VNB 50 kg
Product 44.9 kg
Condensate 1.9 kg
Reaction Temperature 160° C. for 17 hours/165° C. for 23 hours
Reaction Time 40 hours
Reaction Pressure Start 12.5 psig/End 7.5 psig
Composition of the reaction mass expressed as GC area % at various reaction times.
The "0" hour was time when reactor reached the target temperature.

|  | Time (hours) | | | | | | | | | | | | |
| --- | --- | --- | --- | --- | --- | --- | --- | --- | --- | --- | --- | --- | --- |
|  | 0 | 8 | 12 | 14 | 16 | 18 | 20 | 22 | 24 | 26 | 28 | 38 | 40 |
| Reactor Pressure (psig) | 12.5 | 11.5 | 10.5 | 10.0 | 9.5 | 9.0 | 8.5 | 8.5 | 8.0 | 8.0 | 7.5 | 7.5 | 7.5 |
| endo-Vinylnorbornene | 73.98 | 36.43 | 19.21 | 14.86 | 10.04 | 7.05 | 4.47 | 4.38 | 2.30 | 1.36 | 0.96 | 0.27 | 0.29 |
| exo-Vinylnorbornene | 17.33 | 18.65 | 18.22 | 17.86 | 16.69 | 16.01 | 15.97 | 15.40 | 14.93 | 14.16 | 13.89 | 12.42 | 12.30 |
| Tetrahydroindene | 6.20 | 36.71 | 50.70 | 54.39 | 56.06 | 58.17 | 62.41 | 60.21 | 63.30 | 63.38 | 64.33 | 65.06 | 65.25 |
| Vinylcyclohexene | 0.27 | 0.25 | 0.27 | 0.27 | 0.28 | 0.28 | 0.29 | 0.28 | 0.29 | 0.29 | 0.30 | 0.32 | 0.32 |
| Butadiene | 0.00 | 0.26 | 0.34 | 0.34 | 0.35 | 0.11 | 0.17 | 0.08 | 0.21 | 0.22 | 0.21 | 0.20 | 0.20 |
| Cyclopentadiene | 0.00 | 0.19 | 0.17 | 0.15 | 0.13 | 0.12 | 0.00 | 0.10 | 0.00 | 0.00 | 0.00 | 0.00 | 0.00 |
| Heavies | 2.22 | 7.51 | 11.08 | 12.14 | 16.45 | 18.26 | 16.69 | 19.55 | 18.98 | 20.59 | 20.31 | 21.73 | 21.63 |
| exo-VNB/Total VNB (%) | 19.0 | 33.9 | 48.7 | 54.6 | 62.4 | 69.4 | 78.1 | 77.9 | 86.7 | 91.2 | 93.5 | 97.9 | 97.7 |

In Run 1, >98% exo-VNB (exo-VNB/Total VNB) was achieved after 20 hours at 180° C., where reactor pressure was incrementally decreased from 30 to 24 psig. The GC data showed that the final ratio of exo-VNB to VCH was 89.55% to 10.45%, indicating that approximately 27% of the initial quantity of exo-VNB could be recovered.

Analysis of the data using first order kinetics shows that the reaction rate for the disappearance of endo-VNB is 7.9E-05 $s^{-1}$ and for exo-VNB is 1.1 E-05 $s^{-1}$. Thus, at 180° C. both species are reacting or isomerizing and endo-VNB is rearranging at a rate approximately 7.2 times faster than the decomposition of exo-VNB.

In Run 2, >98% exo-VNB was achieved after 12 hours at 180° C., where reactor pressure was incrementally decreased from 28 to 21 psig. The GC data showed that the final ratio of exo-VNB to VCH was 92.80% to 7.20%, indicating that approximately 37% of the initial quantity of exo-VNB could be recovered.

Analysis of the data using first order kinetics shows that the reaction rate for the disappearance of endo-VNB is 1.2E-04 $s^{-1}$ and for exo-VNB is 1.7E-05 $s^{-1}$. Thus, at 180° C. both species are reacting or isomerizing and endo-VNB is rearranging at a rate approximately 7.1 times faster than the decomposition of exo-VNB.

In Run 3, ~98% exo-VNB was achieved after 38 hours at 160-165° C., where reactor pressure was incrementally decreased from 12.5 to 7.5 psig. The GC data showed that the final ratio of exo-VNB to VCH was 97.46% to 2.54%, indicating that approximately 67% of the initial quantity of exo-VNB could be recovered.

Analysis of the data using first order kinetics enabled two reaction rates to be determined for the two reaction temperatures. At 165° C., the reaction rate for the disappearance of endo-VNB is 1.19E-04 $s-1$ and for exo-VNB is 1.67E-05 $s^{-1}$. Thus, at 165° C. both species are reacting or isomerizing and endo-VNB is rearranging at a rate about 18 times faster than the decomposition of exo-VNB.

At 160° C., the reaction rate for the disappearance of endo-VNB is 3.21E-05 $s^{-1}$ and for exo-VNB is 4.18E-07 $s^{-1}$. Thus, at 160° C. both species are reacting or isomerizing and endo-VNB is rearranging at a rate about 76.82 times faster than the decomposition of exo-VNB. It is preferred to have the exo-VNB species decreasing at a rate that is significantly slower than the Cope rearrangement of endo-VNB causes the endo-VNB to disappear. With respect to the quality of the exo-VNB generated, the table below shows the % VCH related to the exo-VNB and endo-VNB in the final mixture. It can be clearly seen that by venting the reactor the VCH concentration is lower and that by running at a temperature where the rate of exo-VNB decomposition is reduced then a much purer product is obtained versus the closed reactor.

|  | Exo-VNB | Endo-VNB | % VCH vs exo-VNB |
| --- | --- | --- | --- |
| Run 1 | 98.6% | 1.4% | 10.4% |
| Run 2 | 98.7% | 1.3% | 7.2% |
| Run 3 | 97.9% | 2.1% | 2.5% |

Additionally, the results of these experiments indicate that the generation of heavy components is reduced if the BD and CPD concentrations are kept low using controlled venting of the reactor.

Example 13

Distillation of High Purity, Exo-Vinylnorbornene

Crude exo-VNB from Run 3 of Example 12 was charged to a vacuum distillation setup consisting of the following equipment: still pot with heating mantle, packed distillation column (60 theoretical plates), reflux splitter, water cooled condenser, condensate receiver and vacuum pump. Still pot temperature was controlled by adjusting the power input to the heating mantle and system vacuum was controlled by adjusting the vacuum pressure at the overhead receiver.

After completing the transfer of 13.9 Kg of crude VNB to the still pot, the distillation system vacuum was adjusted to the desired set point. Heating of the still pot then proceeded until total reflux conditions were established in the distillation column. The reflux splitter was then started at the desired reflux ratio and fractional distillation proceeded by periodically removing liquid fractions from the overhead receiver. GC analysis was used to determine composition of the overhead liquid fractions. Distillation reflux ratio was adjusted as needed to affect composition of the overhead stream. The initial distillation overhead fractions are enriched in the "light" components, which are primarily butadiene (BD), cyclopentadiene (CPD) and vinyl cyclohexene (VCH). After removal of the "light" components, high purity exo-VNB is then separated from the remaining THI. The distillation process is terminated once THI is observed in the overhead stream. Details of the distillation conditions and resultant overhead fractions collected are given in the table below.

| Distillation (Example 12, Run 3 Charged) | | |
| --- | --- | --- |
| Crude VNB Charged | 13.9 kg | |
| Still Pot Temperature | 110° C. | |
| Overhead Temperature | 83° C. | |
| System Vacuum | 28-30 mmHg | |
| Reflux Ratio | 30:1 | |
| Exo-VNB Distillation Material Balance | Weight (kg) | Weight (%) |
| Low Purity Fractions (80-90%) | 0.16 | 1.1 |
| Med Purity Fractions (90-98%) | 0.57 | 4.1 |
| Hi Purity Fractions (>98%) | 0.58 | 4.2 |
| Bottoms | 12.48 | 89.8 |
| Losses | 0.11 | 0.8 |
| Total | 13.9 | |

This experiment showed that approximately 75% of the contained exo-VNB in the crude starting mixture was removed during the fractional distillation. VCH was the main impurity present in the overhead fractions and proved to be difficult to separate from exo-VNB, due to the close boiling points of these materials. GC analysis of the Hi-Purity VNB fractions collected indicated that the exo-VNB content was >98% and the VCH content was <0.25%.

Example 14

Thermolysis of Commercially Available Endo-Exo-Vinylnorbornene (Ineos) Under Back-Pressure Control

Isobaric Reaction

Endo-/exo-VNB (Ineos) (357 g) was added to a 1000 mL three-necked flask fitted with an air cooled column (12 inch height) filled with Pro-Pak® stainless steel packing and vented to an oil bubbler. The endo-/exo-VNB mixture was initially heated in an oil bath set at 141° C. until a 6 inch head of vapor was observed in the packed column. At this vapor head height, the pot temperature was about 142° C. During the course of the experiment, a period of nine days, the temperature of the oil was adjusted to maintain the initial vapor head height after heating for a total of 216 hours, the reaction mixture reached 166° C.

After allowing the reaction mixture to cool to room temperature, it was weighed and found to be 250 g. Next a sample of the mixture was analyzed by GC and determined to have the following ratio of components: 0.05% VCH (essentially unchanged), 23.6% exo-VNB (about 84% of its initial value), and 76.1% THI. This composition represented a ratio of exo-VNB to VCH of 99.8% to 0.20% with no endo-VNB detected. Additionally, neither BD nor CPD were detected in the sample. The level of VCH decreased to about 87% of its initial value and other impurities (which are removable via distillation) increased to 117% of their initial values, and only a small increase in heavies content was observed during the course of the experiment. The details of the experiment are noted in Table 4.

Thus, under the controlled pressure (isobaric) condition of the reaction employed it appears all the butadiene was able to leave the system and so did not combine to form the undesirable VCH byproduct. Additionally, there was no CPD in the sample. A small yield of heavies was noted, but the level is significantly lower than sealed reactions indicating that starting exo-VNB concentration is preserved to a greater extent. Over the experimental temperature range 142-166° C., the rate of disappearance of endo-VNB was determined to be $1.18E\text{-}05 \text{ s}^{-1}$ by analysis of the data using first order kinetics.

In this example, the use of a fractionation process on the vent stream was demonstrated because the boiling reaction mixture was under reflux through a column containing Pro-Pak® packing and only BD and CPD were contained in the collected vent stream samples.

The final reaction mixture (250 grams) was distilled to recover 225.6 grams of a high purity mixture containing exo-VNB and THI. The composition of this material was 23.6% exo-VNB, 0.4% EtNB (ethylnorbornene), 0.1% ENB (ethylidenenorbornene), 0.1% 1,5-COD (1,5-cyclooctadiene), and 75.7% THI.

TABLE 4

Isobaric Thermolysis of Endo-/Exo-VNB (Ineos)
GC Analysis (Area % and Retention Times)

| Time (hrs) | Reaction Temp. (° C.) | VCH 12.04 | Endo-VNB 13.44 | Exo-VNB 13.58 | NBEt 14.11 | ENB 14.33 | 1,5-COD 15.21 | THI 16.72 | Heavies >17.0 |
|---|---|---|---|---|---|---|---|---|---|
| 0 | 141 | 0.06 | 73.51 | 25.85 | 0.33 | 0.1 | 0.11 | 0.05 | 0 |
| 24 | 144 | 0.06 | 58.49 | 27.02 | 0.33 | 0.1 | 0.11 | 13.14 | 0.75 |
| 30 | 149 | 0.06 | 54.52 | 27.23 | 0.34 | 0.11 | 0.11 | 16.73 | 0.92 |
| 47.25 | 153 | 0.06 | 42.76 | 27.91 | 0.34 | 0.11 | 0.11 | 27.43 | 1.28 |
| 53.5 | 155 | 0.06 | 38.48 | 28.25 | 0.34 | 0.11 | 0.11 | 31.16 | 1.5 |
| 71.92 | 157 | 0.06 | 26.84 | 28.79 | 0.34 | 0.11 | 0.12 | 41.96 | 1.79 |
| 74.75 | 157 | 0.06 | 25.1 | 28.69 | 0.34 | 0.11 | 0.12 | 43.62 | 1.97 |
| 77.5 | 158 | 0.06 | 23.61 | 28.84 | 0.34 | 0.11 | 0.12 | 45 | 1.93 |
| 94.5 | 160 | 0.06 | 15.37 | 29.07 | 0.34 | 0.11 | 0.12 | 52.97 | 1.97 |
| 98.83 | 160 | 0.06 | 13.64 | 29.05 | 0.34 | 0.11 | 0.12 | 54.77 | 1.91 |
| 101.42 | 160 | 0.06 | 12.7 | 29.12 | 0.35 | 0.11 | 0.12 | 55.62 | 1.93 |
| 145.5 | 164 | 0.06 | 2.71 | 28.72 | 0.36 | 0.11 | 0.12 | 65.43 | 2.48 |
| 153.5 | 164 | 0.06 | 1.96 | 28.03 | 0.36 | 0.11 | 0.12 | 66.46 | 2.9 |
| 166.28 | 164 | 0.06 | 1.14 | 27.22 | 0.35 | 0.11 | 0.12 | 67.98 | 3.02 |
| 173.75 | 166 | 0.06 | 0.83 | 26.82 | 0.35 | 0.11 | 0.12 | 69.13 | 2.57 |
| 192.25 | 166 | 0.06 | 0.38 | 26.32 | 0.36 | 0.11 | 0.12 | 70.11 | 2.54 |
| 199.25 | 166 | 0.05 | 0.29 | 25.52 | 0.35 | 0.11 | 0.12 | 70.01 | 3.55 |
| 213.67 | 166 | 0.05 | 0.15 | 25.1 | 0.35 | 0.12 | 0.13 | 71.44 | 2.66 |
| 221.5 | 166 | 0.05 | 0.11 | 24.66 | 0.35 | 0.12 | 0.13 | 71.62 | 2.97 |
| 239.5 | 166 | 0.05 | 0.06 | 23.77 | 0.35 | 0.12 | 0.13 | 71.86 | 3.68 |
| 246.25 | 166 | 0.05 | 0 | 23.47 | 0.35 | 0.11 | 0.13 | 71.76 | 4.14 |
| 262.25 | 166 | 0.05 | 0 | 23.09 | 0.35 | 0.12 | 0.13 | 72.27 | 3.99 |
| 270 | 166 | 0.05 | 0 | 22.65 | 0.35 | 0.12 | 0.13 | 73.48 | 3.23 |
| VHC: endo-VNB: exo-VNB: THI | | | 0.05% | 0.00% | 23.55% | | | | 76.13% |
| VCH: exo-VNB | | 0.21% | | 99.79% | | | | | |
| Species (Final)/Species (Initial | | 83.73% | | | 87.61% | 106.78% | 115.33% | 117.71% | |

Example 15

Preparation of High Purity, Exo-VNB from Endo-Exo-Vinylnorbornene (80:20) Under Back-Pressure Control (Isobaric Reaction) and Fractional Distillation Under a nitrogen atmosphere, endo-/exo-VNB (Aldrich) (841 g) was added to a 2000 mL three-necked glass flask fitted with an air cooled glass column (12 inch height) filled with Pro-Pak® stainless steel packing and vented to an oil bubbler. The endo-/exo-VNB mixture was initially heated until about a 6 inch head of vapor was observed in the packed column. The initial pot temperature was about 141° C. After heating for a total of 216 hours, the reaction mixture had a boiling point at 165° C. The weight of the final mixture was 745.5 g (89% recovery) indicating a loss of 95.5 g of by-products. The final reaction mixture was analyzed by proton NMR to determine that no endo-VNB was present at the end of the reaction. A sample of the mixture was analyzed by GC and determined to have the following ratio of components: 0.384% VCH, 26.28% exo-VNB, and 72.17% THI. A sample of exo-VNB was obtained via fractional distillation with a purity of 99.0% with essentially no VCH present. The absence of VCH and endo-VNB in the sample was confirmed by proton NMR.

Example 16

Monitoring of the Generation of a Exo-VNB from Endo-Exo-Vinylnorbornene (82:18) in an Autoclave In this series of four experiments, commercial endo-/exo-VNB (Ineos) was charged to a 300 mL autoclave and heated at temperatures of 165° C. (32 hours), 180° C. (9 hours), 190° C. (8 hours), and 210° C. (3 hours). The heated solutions were sampled periodically and the relative concentrations of endo-VNB, exo-VNB, and THI were measured. From the first order reaction kinetic plots the relative rate constants were derived.

| Reaction Temperature (° C.) | k(endo), s−1 | k(exo), s−1 | k(endo)/k(exo) | Calculated Time to 99% Conversion (hours) | Days |
|---|---|---|---|---|---|
| 165 | 1.92E−05 | 2.68E−07 | 71.57 | 66.78 | 2.78 |
| 180 | 7.56E−05 | 1.73E−06 | 43.76 | 16.92 | 0.70 |
| 195 | 1.21E−04 | 4.06E−06 | 29.78 | 10.59 | 0.44 |
| 210 | 3.88E−04 | 1.90E−05 | 20.41 | 3.29 | 0.14 |

As seen in the above table, the ratio of the rate at which endo-VNB disappears to the rate at which exo-VNB disappears is highest at 165° C. Therefore to maintain the highest possible concentration of exo-VNB in the system a lower temperature must be maintained, (the value of k endo/k exo is maximized).

Example 17

Thermolysis of Endo-/Exo-Vinylnorbornene (82:18) in an Autoclave

In this example, commercial endo-/exo-VNB (Ineos) was charged to a 300 mL autoclave and heated at 150° C. and the pressure in the reactor was allowed to vary based upon the composition of the reactants. At this low temperature (see Table below) the formation of BD, CPD, VCH, DCPD, THI, and heavies are all generated and their concentrations increase from the starting values. Additionally, a significant increase in heavies is observed versus the lower values generated at the near atmospheric thermolysis using controlled venting to enable release of reaction decomposition products (cf. Example 14, Table 4).

| | GC Components (Area %) | | | | | | | |
|---|---|---|---|---|---|---|---|---|
| Time (seconds) | BD | CPD | VCH | VNB | THI | DCPD | Heavies 1 | Heavies 2 |
| 0 | 0 | 0 | 0.2 | 97.65 | 0 | 0.014 | 0 | 0 |
| 19380 | 0.23 | 0.11 | 0.24 | 87.83 | 5.77 | 0.10 | 1.46 | 0 |
| 78780 | 0.37 | 0.098 | 0.26 | 64.65 | 26.83 | 0.29 | 6.54 | 0.097 |
| 165180 | 0.32 | 0.078 | 0.28 | 42.44 | 43.36 | 0.29 | 11.92 | 1.21 |
| 250680 | 0.25 | 0.056 | 0.30 | 28.78 | 52.83 | 0.20 | 15.17 | 2.32 |

Example 18

Thermolysis of Endo-Exo-Vinylnorbornene Under Back-Pressure Control

Ramped Temperature and Pressure Reaction

Endo-/exo-vinyl norbornene (Ineos) was weighed into a batch reactor system consisting of the following major equipment: pressure-rated glass reactor, temperature controlled oil bath, and overhead condensate receiver tank. Reactor temperature was automatically controlled using an external hot oil bath; reactor pressure was manually controlled using a back-pressure control valve on the reactor vent line connected to the overhead receiver. The initial ratio of VNB exo/endo isomers was 25% exo-VNB to 75% endo-VNB.

Oxygen was removed from the reactor headspace using three pressure/vacuum swings with nitrogen. After this nitrogen purge process, the reactor was pressurized with nitrogen to the desired initial setpoint at ambient temperature (20° C.). The reactor content was rapidly heated to the desired initial temperature. The reaction was continued at the initial temperature for the required time, and the system pressure control setpoint was decreased incrementally throughout the first reaction period. Reaction temperature was then decreased rapidly to the second temperature setpoint. The reaction was continued at the second temperature for the required time, and the system pressure control setpoint was again decreased incrementally throughout the second reaction period. Vapor released from the reactor was condensed and collected in the overhead condensate tank.

Run 1
Reactor Charge: VNB 150 gm
Reactor Discharge: 141 gm
Condensate/Losses: 9 gm
Reaction Temperature: First Stage 165° C., Second Stage 155° C.
Total Reaction Time: 140 hours (18 hours at 165° C./122 hours at 155° C.)
Reaction Pressure: Start 12 psig/End 4 psig
Composition of the reaction mass expressed as GC area % at various reaction times.
The "0" hour was time when reactor reached the target temperature.

| | Time (hours) | | | | | | | | |
|---|---|---|---|---|---|---|---|---|---|
| | 0 | 3 | 19 | 28 | 43 | 51 | 67 | 76 | 140 |
| Reactor Temperature(° C.) | 159 | 164 | 155 | 155 | 156 | 156 | 156 | 156 | 156 |
| Reactor Pressure (psig) | 12 | 12 | 10 | 7 | 6 | 5 | 4 | 4 | 4 |
| endo-Vinylnorbornene | 71.11 | 54.50 | 20.69 | 7.32 | 3.18 | 2.21 | 1.20 | 0.85 | 0.08 |
| exo-Vinylnorbornene | 26.00 | 27.32 | 28.70 | 27.91 | 26.66 | 26.14 | 25.21 | 24.72 | 21.15 |
| Tetrahydroindene | 1.97 | 16.75 | 48.67 | 63.17 | 68.85 | 70.34 | 72.31 | 73.14 | 77.26 |
| Vinylcyclohexene | 0.01 | 0.01 | 0.06 | 0.09 | 0.11 | 0.11 | 0.12 | 0.12 | 0.15 |
| Heavies | 0.01 | 0.30 | 0.40 | 0.33 | 0.22 | 0.20 | 0.20 | 0.19 | 0.23 |
| exo-VNB/Total VNB (%) | 26.8 | 33.4 | 58.1 | 79.2 | 89.3 | 92.2 | 95.5 | 96.7 | 99.6 |

Run 2
Reactor Charge: VNB 150 gm
Reactor Discharge: 140 gm
Condensate/Losses: 10 gm
Reaction Temperature: First Stage 170° C., Second Stage 160° C.
Reaction Time: 100 hours (40 hours at 170° C./60 hours at 160° C.)
Reaction Pressure: Start 11 psig/End 2 psig
Composition of the reaction mass expressed as GC area % at various reaction times.
The "0" hour was time when reactor reached the target temperature.

| | Time (hours) | | | | | | | | | |
|---|---|---|---|---|---|---|---|---|---|---|
| | 0 | 3 | 18 | 27 | 42 | 50 | 66 | 74 | 90 | 100 |
| Reactor Temperature(° C.) | 168 | 170 | 172 | 172 | 161 | 162 | 161 | 162 | 162 | 162 |
| Reactor Pressure (psig) | 11 | 11 | 11 | 11 | 4.5 | 2.5 | 2.5 | 2.5 | 2.0 | 2.0 |
| endo-Vinylnorbornene | 70.83 | 57.74 | 16.72 | 5.17 | 0.99 | 0.44 | 0.24 | 0.15 | 0.14 | 0.13 |
| exo-Vinylnorbornene | 26.09 | 27.14 | 27.20 | 23.58 | 21.15 | 19.97 | 18.77 | 17.78 | 16.59 | 15.81 |
| Tetrahydroindene | 2.13 | 13.91 | 54.26 | 69.58 | 76.10 | 77.85 | 79.24 | 80.35 | 81.55 | 82.17 |
| Vinylcyclohexene | 0.01 | 0.01 | 0.11 | 0.23 | 0.31 | 0.34 | 0.37 | 0.39 | 0.41 | 0.43 |
| Heavies | 0.01 | 0.15 | 0.30 | 0.25 | 0.23 | 0.23 | 0.23 | 0.23 | 0.23 | 0.23 |
| exo-VNB/Total VNB (%) | 26.9 | 32.0 | 61.9 | 82.0 | 95.5 | 97.8 | 98.7 | 99.2 | 99.2 | 99.2 |

In Run 1, 99% exo-VNB was achieved after 140 hours of total reaction time, where the first 18 hours was at 165° C. and the remaining 122 hours was at 155° C. and where reactor pressure was incrementally decreased from 12 to 4 psig. The GC data showed that the final ratio of exo-VNB to VCH was 99.30% to 0.70%, indicating that approximately 85% of the initial quantity of exo-VNB could be recovered. Analysis of the data using first order kinetics enabled two reaction rates to be determined for the two reaction temperatures. At 165° C., the reaction rate for the disappearance of endo-VNB is 1.72E-05 s$^{-1}$ and for the formation of exo-VNB is 1.35E-06 s$^{-1}$. At 155° C., the reaction rate for the disappearance of endo-VNB is 1.12E-05 s$^{-1}$ and for exo-VNB is 6.87E-07 s$^{-1}$. Thus, at 155° C. both species are reacting or isomerizing and endo-VNB is rearranging at a rate 16.3 times faster than the decomposition of exo-VNB.

In Run 2, >99% exo-VNB was achieved after 74 hours of total reaction time, where the first 40 hours was at 170° C. and the remaining 34 hours was at 160° C. and where reactor pressure was incrementally decreased from 11 to 2 psig. The GC data showed that the final ratio of exo-VNB to VCH was 97.85% to 2.15%, indicating that approximately 71% of the initial quantity of exo-VNB could be recovered. Analysis of the data using first order kinetics enabled two reaction rates to be determined for the two reaction temperatures. At 170° C., the reaction rate for the disappearance of endo-VNB is 2.52E-05 s$^{-1}$ and for exo-VNB is 6.95E-07 s$^{-1}$. At 160° C., the reaction rate for the disappearance of endo-VNB is 1.54E-05 s$^{-1}$ and for exo-VNB is 1.38E-06 s$^{-1}$. Thus, at 160° C. both species are reacting or isomerizing and endo-VNB is rearranging at a rate 11.2 times faster than the decomposition of exo-VNB.

Example 19

Thermolysis of Endo-Exo-Vinylnorbornene Under Back-Pressure Control

Ramped Temperature and Pressure Within Separation Column

Endo-/exo-vinyl norbornene (Ineos) was weighed into a batch distillation unit consisting of the following major equipment: jacketed still pot, column containing 12 theoretical stages of structured packing, dual overhead condensers and overhead condensate receiver tank. Still pot jacket temperature was automatically controlled using a dedicated hot oil unit; system pressure was automatically controlled using a split range control scheme, with nitrogen addition to increase pressure and vent takeoff to decrease pressure on the overhead receiver. The initial ratio of VNB exo/endo isomers was 25% exo-VNB to 75% endo-VNB.

Oxygen was removed from the distillation system using three pressure/vacuum swings with nitrogen. After this nitrogen purge process, the distillation unit was left under vacuum (−10 psig) and ambient temperature (20° C.). The still pot content was rapidly heated to the desired initial temperature. Initial overhead receiver pressure control set point was input once the system pressure reached o psig during the heat-up. The reaction was continued at the initial temperature for the required time, and the system pressure control set point was decreased incrementally throughout the first reaction period. Reaction temperature was then decreased rapidly to the second temperature set point. The reaction was continued at the second temperature for the required time, and the system pressure control set point was again decreased incrementally throughout the second reaction period. Vapor released from the still pot through the distillation column was condensed and collected in the overhead receiver tank.

retical stages of random packing) reflux splitter, water cooled condenser, condensate receiver and vacuum pump. Still pot temperature was controlled by adjusting the heat input to the jacket and the system vacuum was controlled by adjusting the vacuum pressure at the overhead receiver. After transferring a known weight of crude exo-VNB to the still pot, the distillation system vacuum was adjusted to the desired set point. Heating of the still pot then proceeded until total reflux conditions were established in the distillation column. The reflux splitter was then started at the desired reflux ratio and fractional distillation proceeded by periodically removing liquid fractions from the overhead receiver. GC analysis was used to determine composition of the overhead liquid fractions collected. Distillation reflux ratio was adjusted as needed to affect composition of the overhead stream. The initial overhead fractions are enriched in the "light" components, which are primarily butadiene (BD), cyclopentadiene (CPD) and vinyl cyclohexene (VCH). After removal of the "light" components, high purity exo-VNB is then separated from the remaining THI. The distillation process is terminated once THI is observed in the overhead stream.

Run 1
Still Pot Charge: VNB 185.7 kg
Still Pot Discharge: 180.0 kg
Condensate/Losses: 5.7 kg
Reaction Temperature: First Stage 165° C., Second Stage 155° C.
Total Reaction Time: 88 hours (20 hours at 165° C./68 hours at 155° C.)
Reaction Pressure: Start 13 psig/End 0 psig
Composition of the reaction mass expressed as GC area % at various reaction times.
The "0" hour was time when reactor reached the target temperature.

| | Time (hours) | | | | | | | | | | | | |
|---|---|---|---|---|---|---|---|---|---|---|---|---|---|
| | 0 | 7 | 16 | 20 | 24 | 31 | 40 | 48 | 55 | 64 | 72 | 79 | 88 |
| Still Pot Temperature(° C.) | 164 | 165 | 166 | 167 | 155 | 156 | 156 | 156 | 156 | 156 | 156 | 156 | 67 |
| Still Pot Pressure (psig) | 13.0 | 13.9 | 13.7 | 6.4 | 0.0 | 0.0 | 0.0 | 0.0 | 0.0 | 0.0 | 0.0 | 0.0 | 0.0 |
| endo-Vinylnorbornene | 71.78 | 39.90 | 6.24 | 3.57 | 2.63 | 1.84 | 1.09 | 0.69 | 0.49 | 0.32 | 0.22 | 0.17 | 0.16 |
| exo-Vinylnorbornene | 24.09 | 26.33 | 25.42 | 24.57 | 24.16 | 23.71 | 23.09 | 22.55 | 22.06 | 21.46 | 20.94 | 20.35 | 20.48 |
| Tetrahydroindene | 2.99 | 31.75 | 66.34 | 69.99 | 71.65 | 72.84 | 74.24 | 75.17 | 75.96 | 76.75 | 77.33 | 77.76 | 77.84 |
| Vinylcyclohexene | 0.03 | 0.06 | 0.18 | 0.21 | 0.22 | 0.22 | 0.22 | 0.23 | 0.23 | 0.23 | 0.24 | 0.25 | 0.24 |
| Butadiene | 0.09 | 0.38 | 0.49 | 0.32 | 0.17 | 0.12 | 0.12 | 0.13 | 0.14 | 0.14 | 0.15 | 0.15 | 0.15 |
| Cyclopentadiene | 0.12 | 0.19 | 0.12 | 0.10 | 0.06 | 0.05 | 0.04 | 0.04 | 0.04 | 0.04 | 0.04 | 0.05 | 0.04 |
| Heavies | 0.03 | 0.47 | 0.35 | 0.33 | 0.24 | 0.36 | 0.34 | 0.32 | 0.20 | 0.19 | 0.19 | 0.19 | 0.19 |
| exo-VNB/Total VNB (%) | 25.1 | 39.8 | 80.3 | 87.3 | 90.2 | 92.8 | 95.5 | 97.0 | 97.8 | 98.5 | 99.0 | 99.2 | 99.2 |

This experiment shows that >99% exo-VNB was achieved after 72 hours of total reaction time, where the first 20 hours was at 165° C. and the remaining 52 hours was at 155° C. and where reactor pressure was incrementally decreased from 13 to 0 psig. The GC data showed that the final ratio of exo-VNB to VCH was 98.87% to 1.13%, indicating that approximately 84% of the initial quantity of exo-VNB could be recovered. Analysis of the data using first order kinetics enabled two reaction rates to be determined for the two reaction temperatures. At 165° C., the reaction rate for the disappearance of endo-VNB is 3.97E-05 $s^{-1}$ and for the formation of exo-VNB is 4.95E-07 $s^{-1}$. At 155° C., the reaction rate for the disappearance of endo-VNB is 1.41E-05 $s^{-1}$ and for exo-VNB is 8.60E-07 $s^{-1}$. Thus, at 155° C. both species are reacting or isomerizing and endo-VNB is rearranging at a rate 16.4 times faster than the decomposition of exo-VNB.

Crude exo-VNB from the above run was charged to a vacuum distillation setup consisting of the following equipment: jacketed still pot, packed distillation column (60 theo-

| Distillation | |
|---|---|
| Crude exo-VNB Charged: | 59.5 kg (39.8% exo-VNB) |
| Still Pot Temperature: | 90-100° C. |
| Overhead Temperature: | 70-75° C. |
| System Vacuum: | 20-25 mmHg |
| Reflux Ratio: | 20:1 |

| Exo-VNB Material Balance | Weight (kg) | Weight (%) |
|---|---|---|
| Low Purity Fractions (80-90%) | 2.6 | 4.4 |
| Medium Purity Fractions ((90-98%) | 7.3 | 12.3 |
| High Purity Fractions (>98%) | 11.5 | 19.3 |
| Bottoms | 37.4 | 62.8 |
| Losses | 0.7 | 1.2 |
| Total | 59.5 | |

This experiment showed that approximately 79% of the contained exo-VNB in the crude starting mixture was removed during the fractional distillation. VCH was the main impurity present in the overhead fractions and proved to be difficult to separate from the exo-VNB, due to the close boiling points of these materials. GC analysis of the high-purity exo-VNB fractions collected indicated that the exo-VNB content was >98% and the VCH content was <0.25%.

Example 20

Preparation of High Purity, Exo-/Endo-Isopropenylnorbornene (MeVNB) (90:10)

Endo-Exo-5-Acetylnorbornene. Cyclopentadiene (308.3 g, 4.7 mol) was freshly cracked from dicyclopentadiene (DCPD) at 38-43° C. and was collected into receivers cooled in dry ice-isopropanol. Methyl vinyl ketone (MVK) (344.2 g, 400 ml, 4.9 mol) was placed in a 4-necked 3-L flask fitted with a condenser, addition funnel, and thermowell. The MVK was magnetically stirred as dropwise addition of cyclopentadiene was started. Addition of cyclopentadiene was stopped when the temperature reached 53° C. and the reaction was then cooled with an ice bath as the temperature surged to 67° C. Addition of cyclopentadiene was resumed when the temperature dropped to 47° C. and the ice bath was removed after the temperature reached 28° C. This addition and cooling cycle was repeated three times. The addition was completed in 78 minutes with temperature ranging from 23 to 71° C. GC analysis after 2.8 hr from the end of addition showed 97% (19:81 exo:endo) product with 2.1% DCPD. The mixture was allowed to stir overnight at room temperature, giving a final product analysis of 93.9% with 1.8% DCPD. The reaction mixture was vacuum distilled through an 18-inch Vigreux column and stillhead fitted with a splitter. The splitter ratio was set to 20:1. Endo-exo-acetylnorbornene (306.5 grams) was obtained having a isomer ratio of 81:19 (endo:exo) and a purity of >99% (0.3% DCPD). GC analysis was done on a DB5 Column, 30 meters, 0.32 mm ID, 0.25 μm film, heat from 45° C. to 200° C. @ 15° C./min, then heat to 300° C. @ 40° C./min., Injector temperature: 275° C., Detector temperature: 350° C., Retention times: 4.65 min (exo), 4.93 min (endo), and 4.30 min DCPD.

Methyltriphenylphosphonium iodide. Triphenylphosphine (1683.8 g, 6.4 mol) was placed in a 4-necked 22-L flask fitted with mechanical stirrer, thermowell, stopper, and nitrogen inlet. 8000 ml of dry toluene was added. The mixture was stirred to dissolve all the triphenylphosphine and caused the temperature to drop to 17° C. Iodomethane (975 g, 6.9 mol) was added. Precipitation of phosphonium salt began immediately. The reaction temperature rose gradually while a very thick white slurry formed. After 40 minutes, the temperature had reached 31.5° C., so the reaction was cooled with a water bath. The temperature slowly dropped back to 30.5° C. after 60 minutes. An additional 1000 ml toluene was added and the mixture was allowed to stir overnight at room temperature. The mixture was filtered and the solids washed with toluene. The resulting 4546 g of damp white solid was placed in a 20-L round bottom flask and rotary evaporated sequentially at 45° C., 50° C., 60° C., 70° C. and then 80° C. Approximately 1.5 L toluene was removed at 45° C. while an additional 500 ml was removed at the higher temperatures. The flask was cooled to 35° C. and the product was rotary evaporated under vacuum overnight. The product was then rotary evaporated at 70-80° C. for two hours and then allowed to cool, while rotary evaporating, to room temperature over 8 hours This yielded 2466 g (95% yield) of dried salt, which showed 0.3 wt % toluene present by NMR. Additional phosphonium salt precipitated from toluene mother liquor within 48 hrs.

Exo enriched Exo-Endo-5-isopropenyl-2-norbornene (MeVNB) Methyltriphenylphosphonium iodide (1364.2 g, 3.4 mol) was slurried in 4000 ml anhydrous diethyl ether in a 4-necked 22-L flask fitted with mechanical stirrer, thermowell, condenser with nitrogen inlet, and stopper. To the stirred slurry was added 5-acetylnorbornene (>99% and averaging 0.3% DCPD, 306.5 g, 2.2 mol). An additional 1000 ml ether was added to rinse in the acetylnorbornene. The reaction mixture was at 18.3° C. when solid potassium tert-butoxide (296.4 g, 2.6 mol) was added portion wise. The mixture immediately yellowed and within 3 minutes warmed to 34.8° C., causing the ether to reflux. The reaction was cooled in an ice-water bath. When ether reflux had subsided, the remaining potassium tert-butoxide was added. Another 1000 ml of ether was added. After one hour, when the reaction had cooled to 25.1° C., GC analysis indicated no remaining 5-acetylnorbornene and 89.3% product (exo/endo ratio=83:17). The mixture was allowed to stir 40 hours, filtered, and washed with ether. The filtrate was rotary evaporated to 545.5 g solid and brown liquid residue. This was filtered and washed exhaustively with pentane until the pentane washes remained clear and precipitated no more solids. The filtrate and washes were rotary evaporated to yield 336 g (>100% crude yield) with 97.4% purity by GC. 1H NMR showed the presence of triphenylphosphine oxide. The crude product was flushed through 612 g silica with pentane. Most product was recovered in the 1st and 2nd 1000 ml pentane flush, yielding 295 g of colorless liquid, 99% purity. GC analysis still showed the presence of triphenylphosphine oxide. The material was loaded onto 783 g silica and flushed with pentane. The first three 1000 ml pentane flushes yielded 258.9 g product of 98.5% purity (exo:endo ratio=83:17) and showing little triphenylphosphine oxide by GC. The product was vacuum distilled through a 12-inch Vigreux column. Pentane and toluene were removed at 24-106° C. (705-141 Torr). Two fractions containing toluene and totaling 39.4 g were collected at 99-105° C. (125-101 Torr). 182 g (60% yield) of 99.3% isopropenylnorbornene was collected at 98-101° C. (100-101 Torr). Exo/endo ratio was 84:16 (GC) and 82:18 (NMR). The product contained 0.6% MeTHI impurity. GC analysis was done on a DB5 Column, 30 meters, 0.32 mm ID, 0.25 μm film, heat from 45° C. to 200° C. @ 15° C./min, then heat to 300° C. @ 40° C./min., Injector temperature: 275° C., Detector temperature: 350° C., Retention times: 3.94 min (exo), 3.98 min (endo) and 4.45 min MeTHI.

In this example, it was found that a high exo-MeVNB (84:16=exo:endo) product containing material is obtained directly via the Wittig reaction of high endo-NBCHO (81:19=endo:exo) starting material with methyltriphenylphosphonium iodide in the presence of base (KO-tert-Bu). The in-situ epimerization under these conditions means that the base catalyzed equilibration of endo-rich NBCHO to exo-rich NBCHO via NaOEtMeOH described by G. Adames, R. Grigg, and J. N. Grover in Tetrahedron Letters, 4, (1974) pp 363-366 is not necessary for in the synthesis of exo-MeVNB.

Example 21

Thermolysis of Endo-Exo-Isopropenylnorbornene with or Without Back-Pressure Control Constant Temperature For each of the (3) runs listed below, endo-/exo-isopropenylnorbornene (≥98% MeVNB) was weighed into a batch reactor system consisting of the following major equipment:

pressure-rated glass reactor, temperature controlled oil bath, and overhead condensate receiver tank. Initially, the endo-/exo-MeVNB mixture was heated to the target temperature and pressure was adjusted until the reactor liquid was observed to be gently boiling. The mixture was maintained at the target temperature for the required time and pressure was incrementally adjusted to maintain this gentle boiling condition. Details of the isothermal target temperatures and ramped pressure conditions for each run are given in the tables below. The initial ratio of MeVNB exo/endo isomers was either 85% exo-MeVNB to 15% endo-MeVNB or 84% exo-MeVNB to 16% endo-MeVNB.

Run 1 (non-vented)
Reactor Charge: MeVNB 60 gm (85% exo-MeVNB to 15% endo-MeVNB)
Reactor Discharge: 59 gm
Losses: 1 gm
Reaction Temperature: 165° C.
Reaction Time: 30 hours
Reaction Pressure: Start 12 psig with Nitrogen/Maximum 29 psig
Composition of the reaction mass expressed as GC area % at various reaction times.
The "0" hour was time when reactor reached the target temperature.

|  | Time (hours) | | | | | |
| --- | --- | --- | --- | --- | --- | --- |
|  | 0 | 3 | 7 | 21 | 25 | 30 |
| Reactor Temperature(° C.) | 165 | 166 | 166 | 166 | 166 | 166 |
| Reactor Pressure (psig) | 24 | 28 | 29 | 28 | 28 | 26 |
| endo-MeVinylnorbornene | 13.34 | 4.99 | 0.84 | 0.00 | 0.00 | 0.00 |
| exo-MeVinylnorbornene | 82.63 | 83.34 | 82.61 | 79.96 | 78.56 | 77.59 |
| MethylTetrahydroindene | 1.56 | 9.54 | 14.38 | 17.77 | 19.08 | 19.99 |
| Isoprene | 0.09 | 0.39 | 0.52 | 0.63 | 0.65 | 0.65 |
| Cyclopentadiene | 0.13 | 0.23 | 0.21 | 0.19 | 0.19 | 0.18 |
| Dicyclopentadiene | 0.69 | 0.72 | 0.68 | 0.55 | 0.53 | 0.54 |
| Heavies | 0.00 | 0.01 | 0.01 | 0.01 | 0.01 | 0.01 |
| exo-MeVNB/Total MeVNB (%) | 86.1 | 94.3 | 99.0 | 100.0 | 100.0 | 100.0 |

Run 2 (vented)
Reactor Charge: MeVNB 50 gm (84% exo-MeVNB to 16% endo-MeVNB)
Reactor Discharge: 47 gm
Condensate/Losses: 3 gm
Reaction Temperature: 165° C.
Reaction Time: 24 hours
Reaction Pressure: Start 740 mmHg/End 680 mmHg
Composition of the reaction mass expressed as GC area % at various reaction times.
The "0" hour was time when reactor reached the target temperature.

|  | Time (hours) | | | | | | | | |
| --- | --- | --- | --- | --- | --- | --- | --- | --- | --- |
|  | 0 | 1 | 2 | 3 | 4 | 5 | 6 | 7 | 22 |
| Reactor Temperature(° C.) | 165 | 165 | 166 | 165 | 164 | 165 | 165 | 166 | 166 |
| Reactor Pressure (mmHg) | 740 | 690 | 690 | 670 | 670 | 675 | 675 | 685 | 680 |
| endo-MeVinylnorbornene | 13.62 | 9.01 | 6.04 | 3.71 | 2.49 | 1.54 | 1.07 | 0.59 | 0.00 |
| exo-MeVinylnorbornene | 83.31 | 83.76 | 83.84 | 83.95 | 83.96 | 83.90 | 83.84 | 83.80 | 82.64 |
| MethylTetrahydroindene | 2.70 | 7.04 | 9.88 | 12.09 | 13.28 | 14.28 | 14.79 | 15.29 | 17.01 |
| Isoprene | 0.06 | 0.03 | 0.04 | 0.03 | 0.03 | 0.03 | 0.02 | 0.02 | 0.04 |
| Cyclopentadiene | 0.06 | 0.03 | 0.05 | 0.05 | 0.05 | 0.05 | 0.04 | 0.04 | 0.05 |
| Dicyclopentadiene | 0.01 | 0.02 | 0.04 | 0.07 | 0.08 | 0.09 | 0.10 | 0.11 | 0.10 |
| Heavies | 0.03 | 0.03 | 0.03 | 0.03 | 0.03 | 0.03 | 0.03 | 0.03 | 0.03 |
| exo-MeVNB/Total MeVNB (%) | 85.9 | 90.3 | 93.3 | 95.8 | 97.1 | 98.2 | 98.7 | 99.3 | 100.0 |

Run 3 (vented)
Reactor Charge: MeVNB 50 gm (84% exo-MeVNB to 16% endo-MeVNB)
Reactor Discharge: 47 gm
Losses: 3 gm
Reaction Temperature: 155° C.
Reaction Time: 27 hours
Reaction Pressure: Start 695 mmHg/End 500 mmHg
Composition of the reaction mass expressed as GC area % at various reaction times.
The "0" hour was time when reactor reached the target temperature.

|  | Time (hours) | | | | | | | | | | |
| --- | --- | --- | --- | --- | --- | --- | --- | --- | --- | --- | --- |
|  | 0 | 1 | 2 | 3 | 4 | 5 | 6 | 7 | 21 | 23 | 26 |
| Reactor Temperature(° C.) | 155 | 156 | 154 | 152 | 153 | 151 | 151 | 151 | 151 | 152 | 151 |
| Reactor Pressure (mmHg) | 695 | 640 | 545 | 520 | 520 | 515 | 515 | 510 | 500 | 500 | 500 |
| endo-MeVinylnorbornene | 14.79 | 10.43 | 8.45 | 7.18 | 6.10 | 5.23 | 4.44 | 3.84 | 0.58 | 0.00 | 0.00 |
| exo-MeVinylnorbornene | 83.29 | 83.54 | 83.73 | 83.76 | 83.80 | 83.81 | 83.89 | 83.85 | 83.73 | 84.06 | 83.85 |
| MethylTetrahydroindene | 1.68 | 5.79 | 7.62 | 8.89 | 9.93 | 10.79 | 11.51 | 12.15 | 15.47 | 15.76 | 15.99 |
| Isoprene | 0.03 | 0.04 | 0.02 | 0.01 | 0.01 | 0.00 | 0.00 | 0.00 | 0.00 | 0.00 | 0.00 |
| Cyclopentadiene | 0.04 | 0.04 | 0.02 | 0.01 | 0.01 | 0.01 | 0.01 | 0.00 | 0.00 | 0.00 | 0.00 |
| Dicyclopentadiene | 0.01 | 0.01 | 0.02 | 0.02 | 0.02 | 0.01 | 0.01 | 0.01 | 0.01 | 0.01 | 0.01 |
| Heavies | 0.03 | 0.03 | 0.03 | 0.03 | 0.03 | 0.03 | 0.03 | 0.03 | 0.03 | 0.03 | 0.03 |
| exo-MeVNB/Total MeVNB (%) | 84.9 | 88.9 | 90.8 | 92.1 | 93.2 | 94.1 | 95.0 | 95.6 | 99.3 | 100.0 | 100.0 |

Run 1 showed that >99% exo-MeVNB was achieved after 7 hours of reaction time at 165° C. The GC data showed that the final ratio of exo-MeVNB to DCPD was 99.2% to 0.8%, indicating that approximately 97% of the initial quantity of exo-MeVNB could be recovered. Analysis of the data using first order kinetics enabled the reaction rates to be determined. At 165° C., the reaction rate for the disappearance of endo-MeVNB is 1.04E-04 $s^{-1}$ and for exo-MeVNB is 6.6E-07 $s^{-1}$. Thus, at 165° C. both species are reacting or isomerizing and endo-MeVNB is rearranging at a rate 156.7 times faster than the decomposition of exo-MeVNB.

Run 2 showed that >99% exo-MeVNB was achieved after 7 hours of reaction time at 165° C., where reactor pressure was incrementally decreased from 740 to 680 mmHg. The GC data showed that the final ratio of exo-MeVNB to DCPD was 99.3% to 0.7%, indicating that approximately 99% of the initial quantity of exo-MeVNB could be recovered. Analysis of the data using first order kinetics enabled the reaction rates to be determined. At 165° C., the reaction rate for the disappearance of endo-MeVNB is 1.1E-04 $s^{-1}$ and for exo-MeVNB is 1.25E-07 $s^{-1}$. Thus, at 165° C. both species are reacting or isomerizing and endo-MeVNB is rearranging at a rate 900 times faster than the decomposition of exo-MeVNB.

Run 3 showed that >99% exo-MeVNB was achieved after 21 hours of reaction time at 155° C., where reactor pressure was incrementally decreased from 695 to 500 mmHg. The GC data showed that the final ratio of exo-MeVNB to DCPD was 99.3% to 0.7%, indicating that approximately 99% of the initial quantity of exo-MeVNB could be recovered. Analysis of the data using first order kinetics enabled the reaction rates to be determined. At 155° C., the reaction rate for the disappearance of endo-MeVNB is 4.E-05 $s^{-1}$ and for exo-MeVNB is 5E-08 $s^{-1}$. Thus, at 155° C. both species are reacting or isomerizing and endo-MeVNB is rearranging at a rate 807 times faster than the decomposition of exo-MeVNB.

By now it should be realized that methods have been described that provide for forming an essentially pure exo-alkenylnorbornene material from an isomeric mixture of an endo- and exo-alkenylnorbornene. These methods are encompassed by embodiments in accordance with the present invention claimed hereinbelow.

For example, in embodiments of the present invention a reaction vessel, which is part of a open reaction system, is charged with an amount of an endo-/exo-alkenylnorbornene mixture. As described, such a reaction system can be configured in a variety of ways that can include one or more devices that include, but are not limited to, a device for providing heating to the reaction vessel, a device for varying the pressure of the vessel and a device for providing an inert gas to the vessel. In addition, the reaction system can encompass condensors, condensate receiver devices, packed or unpacked columns, fractional distillation columns, oil bubblers and the like.

Generally, after charging the reaction vessel, one of the vessel pressure or temperature is fixed and the other is adjusted to allow the vapor pressure of the mixture to be at or slightly below the boiling point of the mixture. Additionally, the temperature of the mixture is effective to allow any endo-alkenylnorbornene present to undergo a Cope rearrangement reaction. As one of skill in the art will understand, as such a Cope rearrangement reaction progresses, a Cope rearrangement product is formed (e.g. for endo-VNB, THI is formed; and for endo-MeVNB, MeTHI is formed) thus changing the composition of initial charge mixture to form a reaction mixture. Such a change in composition will of course change the boiling point of the reaction mixture. Advantageously, embodiments in accordance with the present invention provide for adjusting one of the temperature and pressure of the reaction system to control the vapor pressure to remain at or slightly below the mixture's boiling point.

As mentioned above, the reaction vessel of embodiments in accordance with the present invention is encompassed within an open reaction system. That is to say, a system that allows some components of the reaction mixture to exit the reaction vessel while other components are retained therein. Control of vapor pressure advantageously limits the exiting materials to what has been defined previously as "lights". Retained components are then the alkenylnorbornene isomers present in the mixture as well as those materials previously defined as "heavies". Advantageously, by providing for such lights to exit the reaction vessel, the recombination of these materials to form undesirable materials is reduced or eliminated thus avoiding the complex mixtures that essentially prevent isolation of a high-purity alkenylnorbornene isomer. For example the complex mixtures disclosed in publications such as Titova et. al in *Thermal Isomerization of*

*Vinylnorbornene*" (Zhurnal Organicheskoi Khimii Vol. 7(11), pp. 2286-8 (1971)); Ploss et. al., in "*Cope Rearrangement of 2-(a-alkenyl)bicyclo[2.2.1]hept-5-enes and -bicyclo [2.2.2]oct-5-enes*" (Journal für Praktische Chemie (Leipzig) Vol. 314(3-4), pp. 467-82 (1972)); and Maeda et. al. in "*Rearrangement of 5-vinyl-2-norbornene to 3a,4,7,7a-tetrahydroindene*" (Nippon Kagaku Kaishi, Vol. 8, pp. 1587-9 (1974)), among others.

In some embodiments of the present invention vapor pressure control encompasses, control of a rate of boiling, a condensation rate, a height of a vapor head or the like. While such control can accomplished manually, some embodiments of the present invention encompass one or more devices that provide such control in an automated manner. For example, the reaction system can include one or more sensors that can monitor an appropriate condition (e.g. height of a vapor head and/or concentration of a reaction mixture component) and report the results of such monitoring to another device included in the system that can provide an appropriate control signal to the temperature and/or pressure control systems. Such automated control can be particularly advantageous where a process in accordance with the present invention is a continuous process or a process that takes several days to complete.

What is claimed is:

1. A process for producing high purity exo-alkenylnorbornene (ANB) from an endo/exo-ANB mixture comprising:
   charging the endo/exo-ANB mixture into a reaction vessel;
   heating the endo/exo-ANB mixture to a temperature effective to cause a Cope rearrangement reaction to occur thereby forming a reaction mixture, the Cope rearrangement reaction comprising converting endo-ANB into a Cope rearrangement reaction product, wherein the endo-ANB conversion is at least about 99%;
   controlling vapor pressure of the reaction mixture in an open system to allow release of lights from the open system while retaining in the reaction mixture endo-ANB, exo-ANB, and heavies, said controlling the vapor pressure comprises controlling temperature and pressure of the reaction vessel, the heavies comprising the Cope rearrangement reaction product, such that the reaction products from the lights are reduced by more than 50% when compared with the reaction products formed from the lights when said vapor pressure is not controlled; and
   separating the high purity exo-ANB in the reaction mixture from the retained heavies by distillation.

2. The process of claim 1 where the endo/exo-ANB mixture charged into the reaction vessel comprises an essentially pure endo/exo-ANB mixture.

3. The process of claim 1 where the endo/exo-ANB mixture charged into the reaction vessel comprises an essentially pure endo/exo-ANB mixture and an inert solvent having a boiling point higher than a boiling point of exo-ANB.

4. The process of claim 3 where the inert solvent comprises tetrahydronaphthalene, nonylcyclohexane, octanenitrile, salicylaldehyde, a synthetic oil or a mineral oil.

5. The process of claim 1 where the separated high purity exo-ANB comprises ultra high purity exo-ANB.

6. The process of claim 1 where the separated high purity exo-ANB comprises exo-vinylnorbornene, and the exo-vinylnorbornene comprises less than 0.5% by weight vinylcyclohexene.

7. The process of claim 1 where controlling the vapor pressure comprises holding the temperature constant.

8. The process of claim 7 where the constant temperature is from 145° C. to 165° C.

9. The process of claim 1 where heating comprises heating to a first temperature and subsequently to a second temperature lower than the first temperature.

10. The process of claim 9 where the first temperature and the second temperature are from 145° C. to 165° C.

11. The process of claim 1 where heating comprises heating to a first temperature and subsequently to a second temperature higher than the first temperature.

12. The process of claim 1 where controlling the vapor pressure comprises providing a temperature to allow release of lights from the reactor vessel of the open system.

13. The process of claim 1 where controlling the vapor pressure comprises controlling a pressure applied to the reaction vessel to allow release of lights from the reactor vessel of the open system.

14. The process of claim 13 where controlling the vapor pressure comprises applying essentially atmospheric pressure.

15. The process of claim 1 where controlling the vapor pressure comprises holding the temperature essentially constant while the pressure is varied.

16. The process of claim 1 where the high purity exo-ANB comprises high purity exo-vinylnorbornene, and the high purity exo-vinylnorbornene is separated as a physical mixture with a Cope rearrangement reaction product.

17. The process of claim 1 where the open system comprises a fractionation column.

18. The process of claim 1 where the endo/exo-ANB mixture comprises between 99% by weight exo-ANB to 1% by weight endo-ANB and 1% by weight exo-ANB to 99% by weight endo-ANB.

19. The process of claim 1 where the open system comprises a batch reactor, a semi-batch reactor or a continuous process reactor.

20. A process for producing high purity exo-ANB from an endo-/exo-ANB mixture comprising:
   applying an effective amount of heat and/or pressure to the endo-/exo-ANB mixture in an open system to control vapor pressure to selectively convert endo-ANB into a Cope rearrangement reaction product, the Cope rearrangement reaction comprising converting endo-ANB into a Cope rearrangement reaction product, wherein the endo-ANB conversion is at least about 99%, and to release lights from the endo/exo-ANB mixture, such that the reaction products from the lights are reduced by more than 50% when compared with the reaction products formed from the lights when said vapor pressure is not controlled so as to provide a mixture of high purity exo-ANB and heavies that comprise the Cope rearrangement reaction product.

21. The process of claim 20, where the vapor pressure is controlled to cause a Cope rearrangement reaction to convert endo-ANB into the Cope rearrangement reaction product.

22. The process of claim 20, where the vapor pressure is controlled to release lights comprising at least one of cyclopentadiene, butadiene, or isoprene.

23. The process of claim 20, further comprising separating the high purity exo-ANB from the Cope rearrangement reaction product by distillation.

24. A process for producing high purity exo-alkenylnorbornene (ANB) from an endo/exo-ANB mixture of formula (I) or (II):

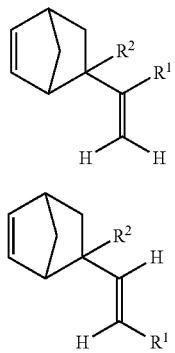

wherein:
$R^1$ is linear or branched $C_2$ to $C_{10}$ alkyl, $C_3$ to $C_8$ cycloalkyl, $C_1$ to $C_{10}$ linear alkyl substituted phenyl; and
$R^2$ is H or Me;

comprising:
charging the endo/exo-ANB mixture into a reaction vessel;
heating the endo/exo-ANB mixture to a temperature effective to cause a Cope rearrangement reaction to occur thereby converting endo-ANB into a Cope rearrangement reaction product;
controlling vapor pressure of the reaction mixture in an open system to allow release of lights from the open system while retaining in the reaction mixture endo-ANB, exo-ANB, and heavies, said controlling the vapor pressure comprises controlling temperature and pressure of the reaction vessel, the heavies comprising the Cope rearrangement reaction product; and
separating the high purity exo-ANB in the reaction mixture from the retained heavies by distillation.

25. The process of claim 24 where the ANB is selected from:
2-(1-propenyl)-5-norbornene,
5-isopropenyl-2-norbornene,
5-(1-methylenepropyl)norbornene,
5-(2-methyl-1-methylenepropyl)norbornene, and
5-(1-phenylethenyl)norbornene.

26. The process of claim 24 where the ANB is 5-isopropenyl-2-norbornene.

* * * * *